US008956867B2

(12) United States Patent
Kamp et al.

(10) Patent No.: US 8,956,867 B2
(45) Date of Patent: Feb. 17, 2015

(54) METHOD FOR CULTURING STEM CELLS

(75) Inventors: Timothy J. Kamp, Madison, WI (US);
Jianhua Zhang, Madison, WI (US);
Jeffrey C. Mohr, Glenview, IL (US);
Juan J. Depablo, Madison, WI (US);
Sean P. Palecek, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 418 days.

(21) Appl. No.: 12/615,044

(22) Filed: Nov. 9, 2009

(65) Prior Publication Data

US 2010/0197013 A1 Aug. 5, 2010

Related U.S. Application Data

(60) Provisional application No. 61/112,368, filed on Nov. 7, 2008.

(51) Int. Cl.
C12N 5/00 (2006.01)
C12N 5/02 (2006.01)
C12N 5/071 (2010.01)
C07K 16/18 (2006.01)
C12N 5/073 (2010.01)

(52) U.S. Cl.
CPC ............. C07K 16/18 (2013.01); C12N 2533/90 (2013.01); C12N 5/0603 (2013.01)
USPC ............ 435/377; 435/395; 435/366; 435/372

(58) Field of Classification Search
USPC .................................... 435/377, 395, 366, 372
See application file for complete search history.

(56) References Cited

U.S. PATENT DOCUMENTS

| | | | |
|---|---|---|---|
| 5,843,780 A | 12/1998 | Thomson | |
| 6,667,176 B1 | 12/2003 | Funk et al. | |
| 2002/0076445 A1 | 6/2002 | Crowe et al. | |
| 2002/0094572 A1 | 7/2002 | Singhvi et al. | |
| 2002/0182188 A1 | 12/2002 | Reid et al. | |
| 2005/0100877 A1 | 5/2005 | Xu et al. | |
| 2005/0164383 A1 | 7/2005 | Reubinoff et al. | |
| 2007/0116680 A1 | 5/2007 | Stegemann | |
| 2008/0026460 A1* | 1/2008 | Palecek et al. ................. | 435/366 |

FOREIGN PATENT DOCUMENTS

| | | |
|---|---|---|
| WO | 96/27287 | 9/1996 |
| WO | 97/39104 | 10/1997 |
| WO | 01/62899 | 8/2001 |
| WO | 2004/098285 | 11/2004 |
| WO | 2005/052138 | 6/2005 |
| WO | 2006/079854 | 8/2006 |

OTHER PUBLICATIONS

Mohr et al. Biomaterials, 27: 6032-6042, 2006.*
Ng et al. Blood, 106(5): 1601-1603, Sep. 2005; available online May 24, 2005.*
Khademhosseini et al. Biomaterials, 27: 5968-5977, 2006.*
Karp et al. Lab Chip, 7: 786-794, May 22, 2007.*
Illi et al. Circulation Research, 96: 501-508, 2005.*
Kim et al. Biosci. Biotechnol. Biochem., 71(12): 2985-2991, Dec. 7, 2007.*
Zandstra et al. Tissue Engineering, 9(4): 767-778, 2003.*
Segev et al. Develop. Growth Differ., 47: 295-306, 2005.*
Anderson D, et al., "Nanoliter-scale synthesis of arrayed biomaterials and application to human embryonic stem cells," Nat. Biotechnol. 22:863-866 (2004).
Chin et al., "Microfabricated platform for studying stem cell fates," Biotech. Bioeng. 88:399-415 (2004).
Clare T, et al., "Functional monolayers for improved resistance to protein adsorption: oligo(ethylene glycol)-modified silicon and diamond surfaces," Langmuir 21:6344-6355 (2005).
Dvash T & Benvenisty N, "Human embryonic stem cells as a model for early human development," Best Pract. Res. Clin. Obstet. Gynaecol. 18:929-940 (2004).
Falconnet D, et al., "Surface engineering approaches to micropattern surfaces for cell-based assays," Biomaterials 27:3044-3063 (2006).
Itskovitz-Eldor J, et al., "Differentiation of human embryonic stem cells into embryoid bodies compromising the three embryonic germ layers," Mol. Med. 6:88-95 (2000).

(Continued)

Primary Examiner — Thaian N Ton
(74) Attorney, Agent, or Firm — Quarles & Brady LLP

(57) ABSTRACT

A three-dimensional microwell system that supports long term pluripotent cell culture and formation of homogeneous embryoid bodies (EBs) is described. Microwell-cultured pluripotent cells remain viable and undifferentiated for several weeks in culture and maintain undifferentiated replication when passaged to Matrigel®-coated, tissue culture-treated polystyrene dishes. Microwell-cultured pluripotent cells maintain pluripotency, differentiating to each of the three embryonic germ layers. Pluripotent cell aggregates released from microwells can be passaged for undifferentiated replication or differentiated to monodisperse EBs. The ability to constrain pluripotent cell growth in three dimensions advantageously provides for more efficient, reproducible culture of undifferentiated cells, high-throughput screening, and the ability to direct pluripotent cell differentiation by generating monodisperse EBs of a desired size and shape. Cardiomyocyte-rich EBs are obtained from pluripotent cells cultured in microwells of defined size and shape.

7 Claims, 14 Drawing Sheets

(56) References Cited

OTHER PUBLICATIONS

Lehnert D, et al., "Cell behaviour on micropatterned substrata: limits of extracellular matrix geometry for spreading and adhesion," J. Cell Sci. 117:41-52 (2004).
Luk Y, et al., "Self-assembled monolayers of alkanethiolates presenting mannitol groups are inert to protein adsorption and cell attachment," Langmuir 16:9604-9608 (2000).
Lussi J, et al., "Pattern stability under cell culture conditions—a comparative study of patterning methods based on PLL-g-PEG background passivation," Biomaterials 27:2534-2541 (2006).
Marple et al., "A genotoxic screen: rapid analysis of cellular dose-response to a wide range of agents that either damage DNA or alter genome maintenance pathways," Mut. Res. 554:253-266 (1994).
Mohr et al., "D-3 microwell culture of human embryonic stem cells," Biomaterials 27:6032-6042 (2006).
Mrksich M, et al., "Controlling cell attachment on contoured surfaces with self-assembled monolayers of alkanethiolates on gold," Proc. Natl. Acad. Sci. USA 93:10775-10778 (1996).
Mrksich M, "Tailored substrates for studies of attached cell culture," Cell Mol. Life Sci. 54:653-662 (1998).
Ng E, et al., Forced aggregation of defined numbers of human embryonic stem cells into embryoid bodies fosters robust, reproducible hematopoietic differentiation, Blood 106:1601-1603 (2005).
Noaksson K, et al., "Monitoring differentiation of human embryonic stem cells using realtime PCR," Stem Cells 23:1460-1467 (2005).
Odorico J, et al., "Multilineage differentiation from human embryonic stem cell lines," Stem Cells 19:193-204 (2001).
Reubinoff B, et al., "Embryonic stem cell lines from human blastocysts: somatic differentiation in vitro," Nat. Biotechnol. 18:399-404 (2000).
Revzin et al., "Surface engineering with poly(ethylene glycol) photolithography to create high-density cell arrays on glass," Langmuir 19:9855-9862 (2003).
Schuldiner M, et al., "Effects of eight growth factors on the differentiation of cells derived from human embryonic stem cells," Proc. Natl. Acad. Sci. USA 97:11307-11312 (2000).
Sidhu K & Tuch B, "Derivation of three clones from human embryonic stem cell lines by FACS sorting and their characterization," Stem Cells Dev. 15:61-69 (2006).
Spradling A, et al., "Stem cells find their niche," Nature 414:98-104 (2001).
Streuli C, "Extracellular matrix remodelling and cellular differentiation," Curr. Opin. Cell Biol. 11:634-40 (1999).
Thomson J, et al., "Embryonic stem cell lines derived from human blastocysts," Science 282:1145-1147 (1998).
Tian X, et al., "Cytokine requirements differ for stroma and embryoid body-mediated hematopoiesis from human embryonic stem cells," Exp. Hematol. 32:1000-1009 (2004).
Wang L, et al., "Endothelial and hematopoietic cell fate of human embryonic stem cells originates from primitive endothelium with hemangioblastic properties," Immunity 21:31-41 (2004).
Watt F & Hogan Bm "Out of Eden: stem cells and their niches," Science 287:1427-1430 (2000).
Wei H, et al., "Embryonic stem cells and cardiomyocyte differentiation: phenotypic and molecular analyses," J. Cell Mol. Med. 9:804-817 (2005).
Whitesides G, et al., "Soft lithography in biology and biochemistry," Annu. Rev. Biomed. Eng. 3:335-373 (2001).
Baust J, et al., "Cell viability improves following inhibition of cryopreservation-induced apoptosis," In Vitro Cell Dev. Biol. Anim. 36:262-270 (2000).
Beattie G, et al., "Trehalose: a cryoprotectant that enhances recovery and preserves function of human pancreatic islets after long-term storage," Diabetes 46:519-523 (1997).
Chen C, et al., "Geometric control of cell life and death," Science 276:1425-1428 (1997).
Chen C, et al, "Micropatterned surfaces for control of cell shape, position, and function," Biotechnol. Prog. 14 356-363 (1998).

Chen C, et al., "Using self-assembled monolayers to pattern ECM proteins and cells on substrates," Methods Mol. Biol. 139:209-219 (1999).
Chen T, et al, "Beneficial effect of intracellular trehalose on the membrane integrity of dried mammalian cells," Cryobiology 43:168-181 (2001).
Conrad P, et al., "Stabilization and preservation of *Lactobacillus acidophilus* in saccharide matrices," Cryobiology 41:17-24 (2000).
Crowe J, et al., "The role of vitrification in anhydrobiosis," Annu. Rev. Physiol. 60:73-103 (1998).
Datta S, et al., "The effect of stabilizing additives on the structure and hydration of proteins: a study involving tetragonal lysozyme," Acta Crystallogr. D. Biol. Crystallogr. 57:1614-1620 (2001).
Derda R, et al., "Defined substrates for human embryonic stem cell growth identified from surface arrays," ACS Chem. Biol. 2:347-355 (2007).
Dusseiller M, et al, "An inverted microcontact printing method on topographically structured polystyrene chips for arrayed micro-3-D culturing of single cells," Biomaterials 26;5917-5925 (2005).
Ekdawi-Sever N, et al., "Molecular simulation of sucrose solutions near the glass transition temperature," J. Phys. Chem. 105:734-742 (2001).
Erdag G, et al., "Cryopreservation of fetal skin is improved by extracellular trehalose," Cryobiology 44:218-228 (2002).
Eroglu A, et al., "Intracellular trehalose improves the survival of cryopreserved mammalian cells," Nat. Biotechnol. 18:163-167 (2000).
Garcia de Castro A & Tunnacliffe A, "Intracellular trehalose improves osmotolerance but not desiccation tolerance in mammalian cells," FEBS Letters 487:199-2002 (2000).
Gearhart J, "New potential for human embryonic stem cells," Science 282:1061-1062 (1998).
Gorlin J, "Stem cell cryopreservation," J. Infus. Chemother. 6:23-27 (1996).
Gulliksson H, "Additive solutions for the storage of platelets for transfusion," Transfus. Med. 10:257-264 (2000).
Heng B, et al., "The cryopreservation of human embryonic stem cells," Biotechnol. Appl. Biochem. 41:97-104 (2005).
Hunt C & Timmons P, "Cryopreservation of human embryonic stem cell lines" Methods Mol. Biol. 368:261-270 (2007).
Ji L, et al., "Cryopreservation of adherent human embryonic stem cells," Biotechnol. Bioeng. 88:299-312 (2004).
Karp J, et al., "Controlling size, shape and homogeneity of embryoid bodies using poly(ethylene glycol) microwells," Lab Chip 7:786-794 (2007).
Katkov, et al., "Cryopreservation by slow cooling with DMSO diminished production of Oct-4 pluripotency marker in human embryonic stem cells," Cryobiology 53:194-205 (2006).
Kaufmann D, et al., "Hematopoietic colony-forming cells derived from human embryonic stem cells," Proc. Natl. Acad. Sci. USA 98:10716-10721 (2001).
Khademhosseini A, et al., "Molded polyethylene glycol microstructures for capturing cells within microfluidic channels," Lab Chip 4:425-430 (2004).
Khademhosseini A, et al., "Cell docking inside microwells within reversibly sealed microfluidic channels for fabricating multiphenotype cell arrays," Lab Chip 5:1380-1386 (2005).
Khademhosseini A, et al., "Microscale technologies for tissue engineering and biology," Proc. Natl. Acad. Sci. USA 103:2480-2487 (2006).
Kim S, et al., "Effects of type IV collagen and laminin on the cryopreservation of human embryonic stem cells," Stem Cells 22:950-961 (2004).
Koebe H, et al., "Cryopreserved porcine hepatocyte cultures," Chem. Biol. Interact. 121:99-115 (1999).
Limaye L & Kale V, "Cryopreservation of human hematopoietic cells with membrane stabilizers and bioantioxidants as additives in the conventional freezing medium," J. Hematother. Stem Cell Res. 10:709-18 (2001).
Liu K, et al., "Comparison of the stress response to cryopreservation in monolayer and three-dimensional human fibroblast cultures: stress proteins, MAP kinases, and growth factor gene expression," Tissue Eng. 6:539-554 (2000).

(56) References Cited

OTHER PUBLICATIONS

Mahler S, et al., "Hypothermic storage and cryopreservation of hepatocytes: the protective effect of alginate gel against cell damages," Cell Transplant. 12:579-592 (2003).

McLellan M & Day J, "Cryopreservation and freeze-drying protocols. Introduction," Methods Mol. Biol. 38:1-5 (1995).

Miller D, et al., "Stabilization of lactate dehydrogenase following freeze thawing and vacuum-drying in the presence of trehalose and borate," Pharm. Res. 15:1215-1221 (1998).

Mrksich M, et al., "Using microcontact printing to pattern the attachment of mammalian cells to self-assembled monolayers of alkanethiolates on transparent films of gold and silver," Exp. Cell Res. 235:305-313 (1997).

Orner B, et al., "Arrays for the combinatorial exploration of cell adhesion," J. Am. Chem. Soc. 126:10808-10809 (2004).

Pera M, et al., "Human embryonic stem cells," J. Cell Sci. 113:5-10 (2000).

Reubinoff B, et al., "Effective cryopreservation of human embryonic stem cells by the open pulled straw vitrification method," Hum. Reprod. 16:2187-2194 (2001).

Saha S, et al., "Inhibition of human embryonic stem cell differentiation by mechanical strain," J. Cell Physiol. 206:126-137 (2006).

Sano F, et al., "A dual role for intracellular trehalose in the resistance of yeast cells to water stress," Cryobiology 39:80-87 (1999).

Singhvi R, et al., "Engineering cell shape and function," Science 264:696-698 (1994).

Suh K, et al., "A simple soft lithographic route to fabrication of poly(ethylene glycol) microstructures for protein and cell patterning," Biomaterials 25:557-563 (2004).

Ure J, et al., "A rapid and efficient method for freezing and recovering clones of embryonic stem cells," Trends Genet. 8:6 (1992).

Voigt M, et al., "Cultured epidermal keratinocytes on a microspherical transport system are feasible to reconstitute the epidermis in full-thickness wounds," Tissue Eng. 5:563-572 (1999).

Weibel D, et al., "Combining microscience and neurobiology," Curr. Opin. Neurobiol. 15:560-567 (2005).

Wolkers W, et al., "Human platelets loaded with trehalose survive freeze-drying," Cryobiology 42:79-87 (2001).

Wolkers W, et al., "From anhydrobiosis to freeze-drying of eukaryotic cells," Comp. Biochem. Physiol. A. Mol. Integr. Physiol. 131:535-543 (2002).

Xu C, et al., "Feeder-free growth of undifferentiated human embryonic stem cells," Nat. Biotechnol. 19:971-974 (2001).

\* cited by examiner

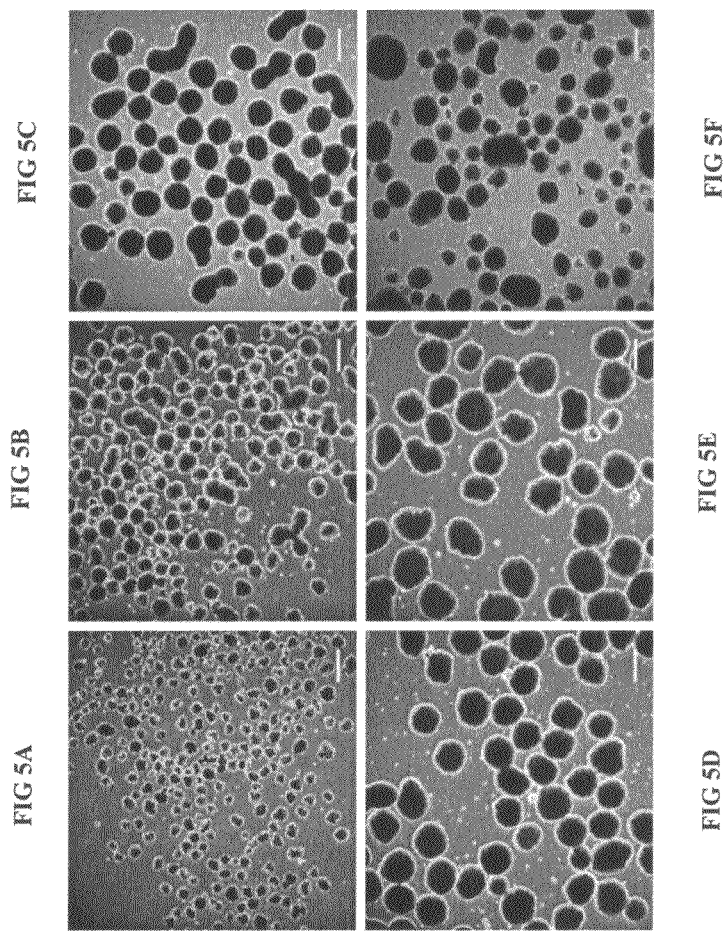

US 8,956,867 B2

METHOD FOR CULTURING STEM CELLS

CROSS-REFERENCE TO RELATED APPLICATIONS

This application claims the benefit of U.S. Provisional Patent Application No. 61/112,368, filed Nov. 7, 2008, incorporated herein by reference as if set forth in its entirety.

STATEMENT REGARDING FEDERALLY SPONSORED RESEARCH OR DEVELOPMENT

This invention was made with government support under contract EB007534 awarded by the National Institutes of Health. The government has certain rights in the invention.

BACKGROUND

Primate embryonic stem (ES) cells and the recently-described induced pluripotent cells (iPS) (collectively, "pluripotent cells") can proliferate without limit and can differentiate into each of the three embryonic germ layers [1-3]. To facilitate self-renewal, primate (including human) pluripotent cells are typically co-cultured with mouse embryonic fibroblast (MEF) feeder cells, or cultured in MEF-conditioned medium (MEF-CM) on a Matrigel® extracellular matrix or in a chemically-defined medium. It is understood that iPS cells behave in culture essentially as do ESC. iPS cells and ESCs express one or more pluripotent cell-specific marker, such as OCT-4, SSEA-3, SSEA-4, TRA-1-60, TRA-1-81, and Nanog. Subsequent references herein to embryonic stem cells, ES cells, human embryonic stem cells, hES cell and the like are intended to apply with equal force to iPS cells.

Cell microenvironment influences embryonic stem (ES) cell differentiation [4, 5]. For example, spontaneous differentiation of ES cell cultures occurs along seemingly random pathways during normal cell culture, especially as colony density and size increase [2, 6]. Typically, however, ES cell differentiation is stimulated either by co-culturing the cells with cells of particular lineages or by chemically or mechanically detaching the cells from their substrate to generate embryoid bodies (EBs) [2] that are cultured in suspension in the absence of MEFs or MEF-CM [7-11]. After several days, EBs in the suspension culture are plated to promote proliferation and further cell differentiation.

Interestingly, EBs in a single culture differentiate to distinct cell lineages. Subtle microenvironment differences in and around individual EBs are thought to affect differentiation of cells in EBs, which then further guide differentiation of other cells by cell-cell contact or by secretion of soluble differentiation factors [6]. One factor that may regulate lineage commitment is EB size [12]. For example, Ng et al. showed efficient generation of hematopoietic cells from "spin EBs" (i.e. EBs generated by centrifugation) having a uniform, yet large size, although the actual number of hES cells aggregating to form these EBs was not known [13]. Smaller spin EBs preferentially differentiated along other lineages. Unfortunately, the art lacks simple methods for producing EBs of consistent and desired size from ES cells.

One way to direct culture of some cell types, including 3T3 fibroblasts [14-17], capillary endothelial cells [18-20], mouse melanoma cells [17] and buffalo rat liver cells [17], is to constrain the cells within a patterned area on a two-dimensional (2-D) monolayer. Micron-scale patterns can be formed in self-assembled monolayers (SAMs) by micro-contact printing alkanethiols that spontaneously assemble via a linkage of a terminal sulfur group to sites on a gold substrate. The SAMs reach equilibrium within one to five hours [19].

Suitable alkanethiols typically contain an eleven to eighteen carbon chain and are capped with a functional group. Depending upon the nature of the functional group, SAMs can attract or repel extracellular matrix (ECM) proteins [16-24]. A common protein-repelling alkanethiol is poly-ethylene glycol (PEG)-terminated alkanethiol containing three to six ethylene glycol groups [16, 20]. Tri-ethylene glycol (EG3)-terminated alkanethiols resist protein and extracellular matrix adsorption for approximately eight days, but thereafter begin to break down under typical cell culture conditions [16]. In contrast, several alkanethiols, including methyl- and amine-terminated molecules, attract extracellular matrix proteins [19, 21, 22, 25-27].

Unfortunately, 2-D SAM monolayers are of limited utility for culturing primate ES cells because of the cell's growth nature. Unlike many cells, primate ES cells, including human ES cells, do not grow to confluence as monolayers and are not contact inhibited, but rather build upon themselves to form cell aggregates [28] that spread beyond the constrained areas of the 2-D monolayers. Likewise, initial efforts at 2-D microcontact printing of Matrigel® on SAM surfaces indicated that this method was not suitable for long-term hES cell culture because of substrate instability and because growing colonies could span across unpatterned regions.

With few exceptions, current literature regarding patterned 2-D monolayers focuses primarily on cell attachment and replication to generate confluent monolayers in patterned regions, but does not investigate effects of three-dimensional confined geometries on long term health and stability of cell lines that are not strictly contact dependent. Orner et. al. [36] discussed hES cell attachment to laminin-derived peptides deposited in 750 µm squares, but the hES cells were only cultured for two days before cellular analysis. After two days, significant spontaneous generation is unlikely to occur even in suboptimal conditions, and no cell characterization data (e.g., differentiation or viability) was presented [32]. Although short-term analysis of selective attachment is useful for screening substrates that permit cell adherence and initial replication, several other requirements exist for use as a robust culture technique with hES cells. That is, hES cells must remain viable, undifferentiated, retain ability for undifferentiated proliferation upon passaging and remain pluripotent. Because hES cell differentiation does not occur immediately, short-term analysis may not accurately represent hES cell response to confinement.

Three-dimensional (3-D) microwells have also been used to study effects of confinement on short-term culture of anchorage-dependent cells. For example, NIH 3T3 fibroblasts were deposited as single cells in microwells 15 µm deep, 75 µm² cross-sectional area [15]. These cells, however, were incubated for only four hours to investigate initial cell attachment and spreading, rather than long-term behavior in microwells. Single epithelial cells were also deposited in 11 µm deep×10 µm lateral microwells. Unfortunately, cell viability after two days was determined solely by visual cell replication [29]. These studies demonstrated the possibility of cell attachment in microwells, but did not show a marked improvement over prior patterned microwells that also constrained cells for at least two days.

BRIEF SUMMARY

In a first aspect, the invention is summarized in that a method for culturing pluripotent cells, including induced pluripotent stem (iPS) cells and ES cells from primates, such as hES cells, includes the step of culturing the cells in a microwell defined in an upper surface of coating on a substrate, the microwell supporting growth of viable, substantially undifferentiated cells that maintain pluripotency in culture for several weeks. Typically, a plurality of microwells is defined in the coating (e.g., as an array). The coating is sufficiently thick that the microwells defined in the coating have measurable dimensions of length, width and depth that define bottom and side wall surfaces.

The bottom surfaces and portions of the side walls proximal to the bottom surfaces are functionalized with a cell-attracting material to form a cell-attracting portion of the microwell, while upper portions of the side walls and the upper coating surface between the microwells are functionalized with a cell-repulsing material to form a cell-repulsing portion. Without limitation, the cell-attracting material can be a functionalized extracellular matrix protein material such as Matrigel®, a viscous protein mixture secreted by murine tumor cells. Likewise, and without limitation, the cell-repulsing material can be a protein-resistant SAM. Advantageously, the cells can grow in all dimensions in the microwells, but not outside of the microwells. Because the cells grow to occupy the defined volume of the microwell, the size and shape of colonies and aggregates attached to the colonies can be controlled. By establishing consistent cell-attracting and cell-repulsing portions of the microwells, the microwells can be dimension-constrained and the colonies and aggregates that grow in the dimension-constrained microwells can be substantially uniform from well to well. In the microwells, the cells remain substantially undifferentiated (i.e. greater than about 90% or between about 90% and about 95% of the cells remain undifferentiated) for at least about three weeks when grown in a non-differentiating medium. The substantially undifferentiated cells retain the ability to self renew and can be plated and passaged like stem cells in conventional culture.

The dimensions of the three-dimensional microwells can be varied as desired or can be uniform from one microwell to another. Microwells of any shape (e.g., round, ovoid and rectangular) are contemplated. The dimensions of the plurality of microwells can be constant (but need not necessarily be equal to one another), such that volume, cell number and shape of colonies cultured in the microwells are substantially consistent among the microwells. Preferably the colonies are monodisperse (i.e. have a narrow size distribution). As used herein, "a narrow size distribution" or "monodisperse" means that the size (i.e. diameter), shape and/or volume of cultured colonies/aggregates within the microwells described herein are within at least 20% of each other, alternatively within at least 15% of each other and alternatively within at least 10% of each other.

In some embodiments, the microwell can have a depth between about 10 μm and about 1000 μm and lateral dimensions (i.e. length and width) between about 50 μm and about 1000 μm on a side, and alternatively can be between about 100 μm and about 500 μm on a side. In certain embodiments, the lateral dimensions of the microwell are substantially identical. Volume per microwell can be consistent, while the dimensions can vary from well to well.

In a second aspect, the invention is summarized in that a method for forming EBs having a narrow size distribution includes the steps of harvesting substantially undifferentiated ES cells or iPS cells from the microwells and culturing the harvested cells under differentiating culture conditions until the culture contains differentiated cells. Because the undifferentiated pluripotent cells for use in the EB-forming method can be obtained from dimension-constrained microwells having uniform dimensions, supra, aggregates having a narrow size distribution can be harvested, thereby avoiding a shortcoming of existing EB-forming methods, namely that clumps of pluripotent cells from which EBs are now derived can vary widely in size, volume and cell number. The harvesting step can include harvesting entire colonies or harvesting cell aggregates anchored to colonies in the microwells but unattached to the coating. Colonies can be released by enzymatic treatment. Aggregates can be released from the colonies by gentle shearing without dislodging the colonies, which can be cultured again to yield more cell aggregates. Aggregates released by gentle shearing have a narrow size distribution and yield cultured EBs also having a narrow size distribution. Where the entire culture is inadvertently harvested during the shearing step, the resulting EB is substantially larger than the majority of the EBs and can be discarded or ignored. Advantageously, the cell differentiation profile of EBs can be controlled by controlling the size, shape, and volume of the undifferentiated cell cultures that give rise to the EBs.

In a third aspect, the invention is summarized in that a method of cryopreserving pluripotent cells includes freezing substantially undifferentiated, microwell-cultured pluripotent cells as described above. In some embodiments of the third aspect, the microwells are rectangular and have a depth between about 10 microns and about 1000 microns with lateral dimensions between about 50 microns and about 600 microns.

In a fourth aspect, the invention is summarized as cell populations of undifferentiated colonies or EBs having substantially uniform size and shape. In some embodiments of the fourth aspect, the colonies or cell populations have rectangular lateral dimensions between about 50 microns and about 600 microns and depth between about 10 microns and about 1000 microns.

In a fifth aspect, the invention is summarized in that a method for culturing pluripotent cells includes culturing substantially undifferentiated pluripotent cells in a dimension-constrained microwell without subculture for at least about three weeks in a medium that does not promote differentiation, wherein greater than about 90% of the cells remain undifferentiated after about three weeks.

BRIEF DESCRIPTION OF THE DRAWINGS

FIG. 5A-F illustrate the sizes of hES cell EBs formed from microwells. EBs were formed following one day of suspension culture from hES cells cultured in microwells of 100 μm (FIG. 5A), 200 μm (FIG. 5B), 300 μm (FIG. 5C), 400 μm (FIG. 5D), and 500 μm (FIG. 5E) lateral dimensions and 120

μm depth compared to EBs from standard culture conditions (FIG. 5F). The scale bars represent 300 μm.

Figures 6A, 6B, 6C, 6D:
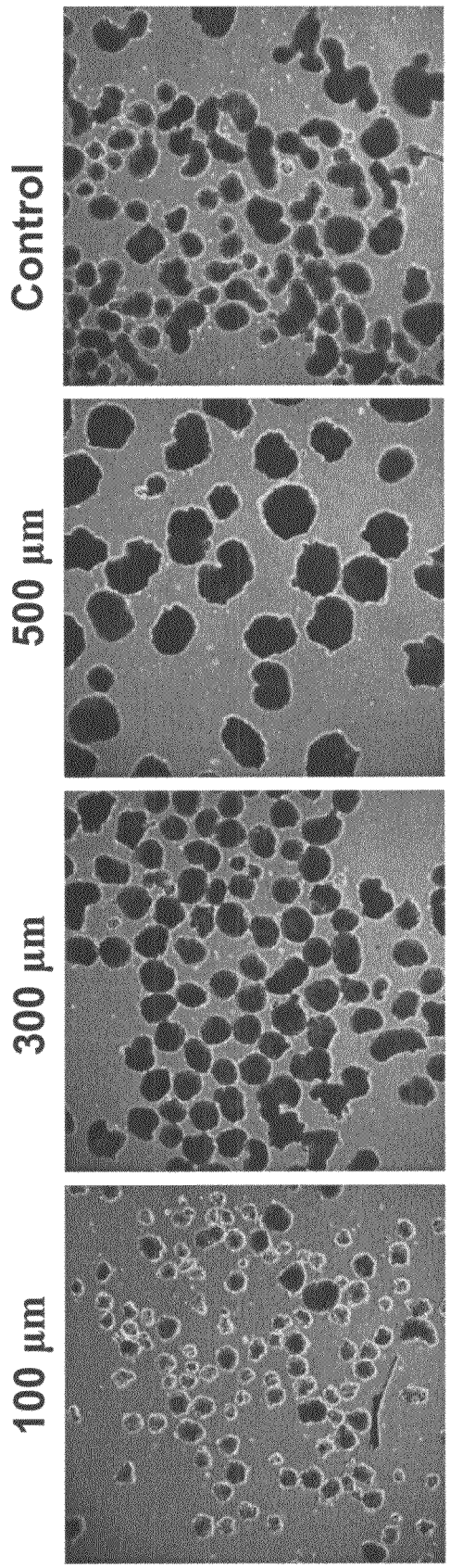

FIG. 6A-D illustrate the sizes of iPS cell EBs formed from microwells. EBs were formed following one day of suspension culture from hES cells cultured in microwells of 100 μm (FIG. 6A), 300 μm (FIG. 6B), and 500 μm (FIG. 6C) lateral dimensions and 120 μm depth compared to EBs from standard culture conditions (FIG. 6D).

Figure 7A:
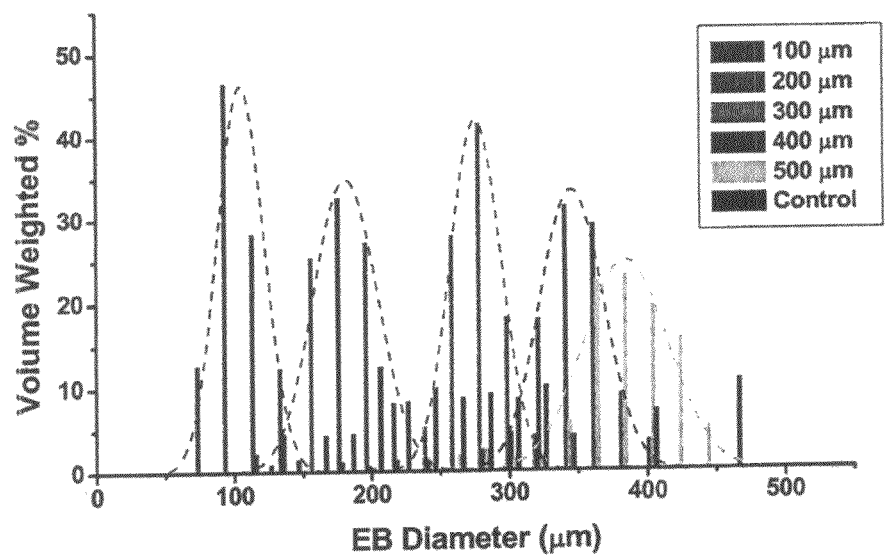
Figure 7B:
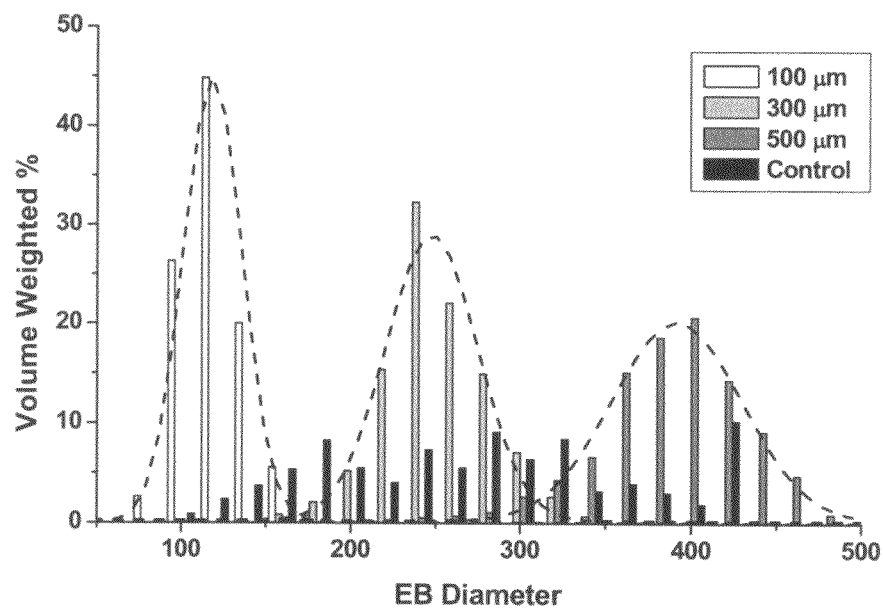
Figure 7C:
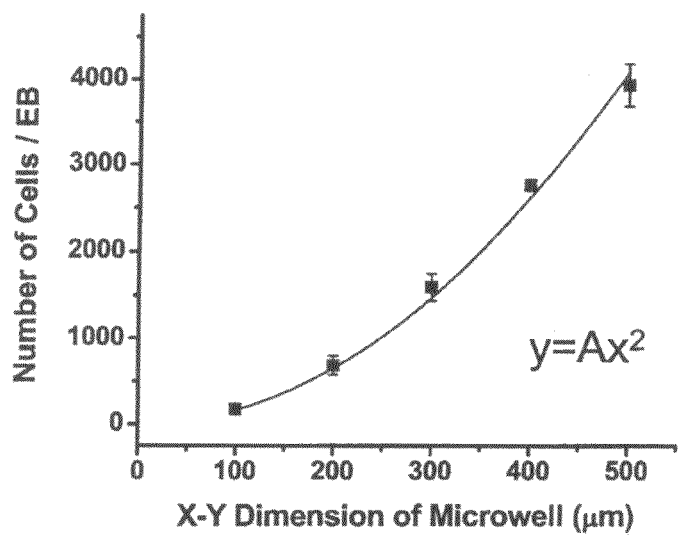

FIG. 7A-C illustrate the sizes and cell numbers of EBs formed from microwells. The histograms show the volume-weighted distribution of hES cell (FIG. 7A) and iPS cell (FIG. 7B) EB sizes, respectively, relative to EB diameter for microwells 120 μm deep×100-500 μm lateral dimension. FIG. 7C shows the number of hES cells per EB formed from microwells 120 μm deep×100-500 μm lateral dimension.

Figure 8A:
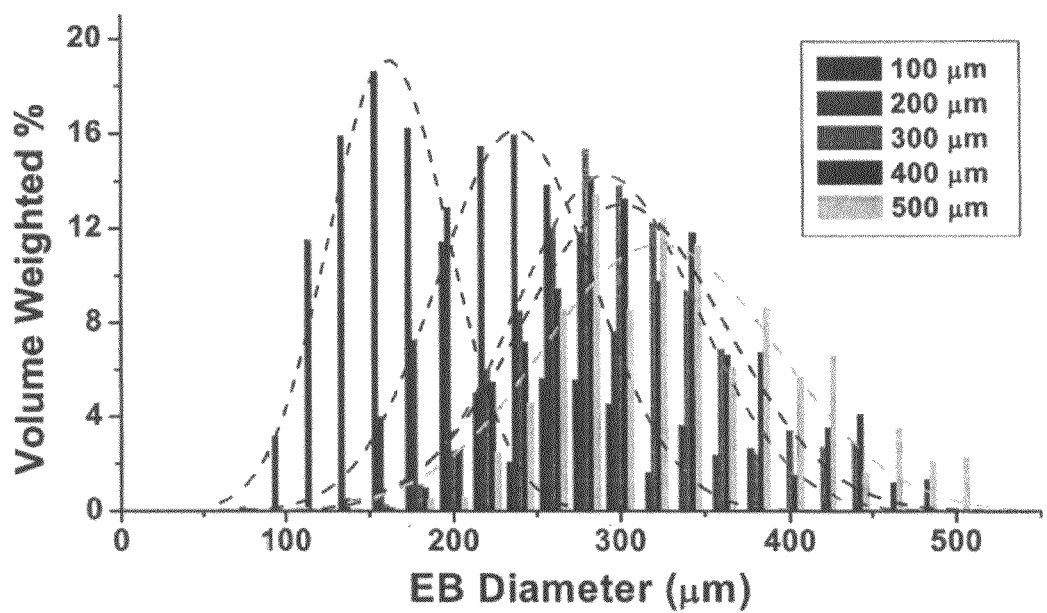
Figure 8B:
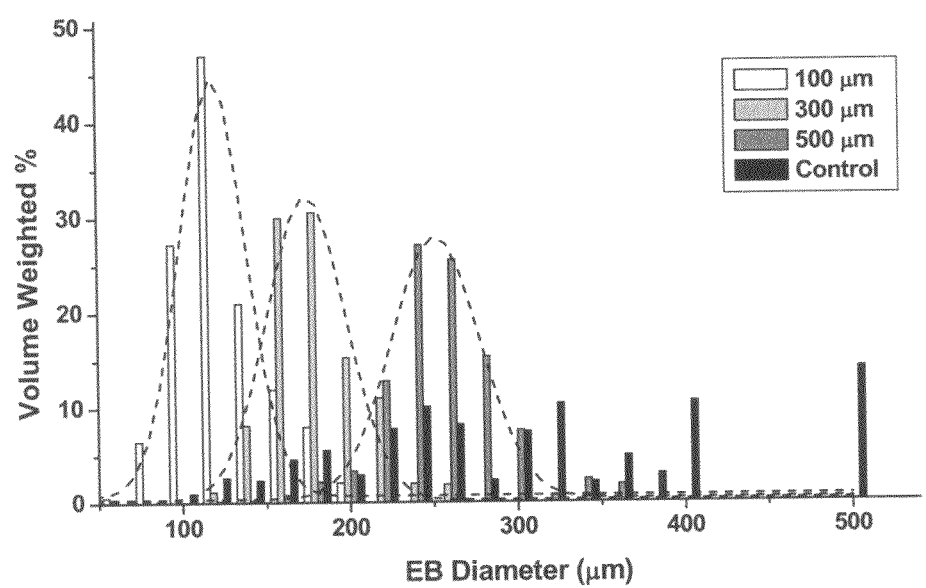

FIG. 8A-B illustrate the volume-weighted size distribution of hES cell EB size (FIG. 8A) and iPS cell EB size (FIG. 8B) relative to EB diameter for microwells 120 μm deep×100-500 μm lateral dimension after 5 days in suspension culture.

Figure 9A:
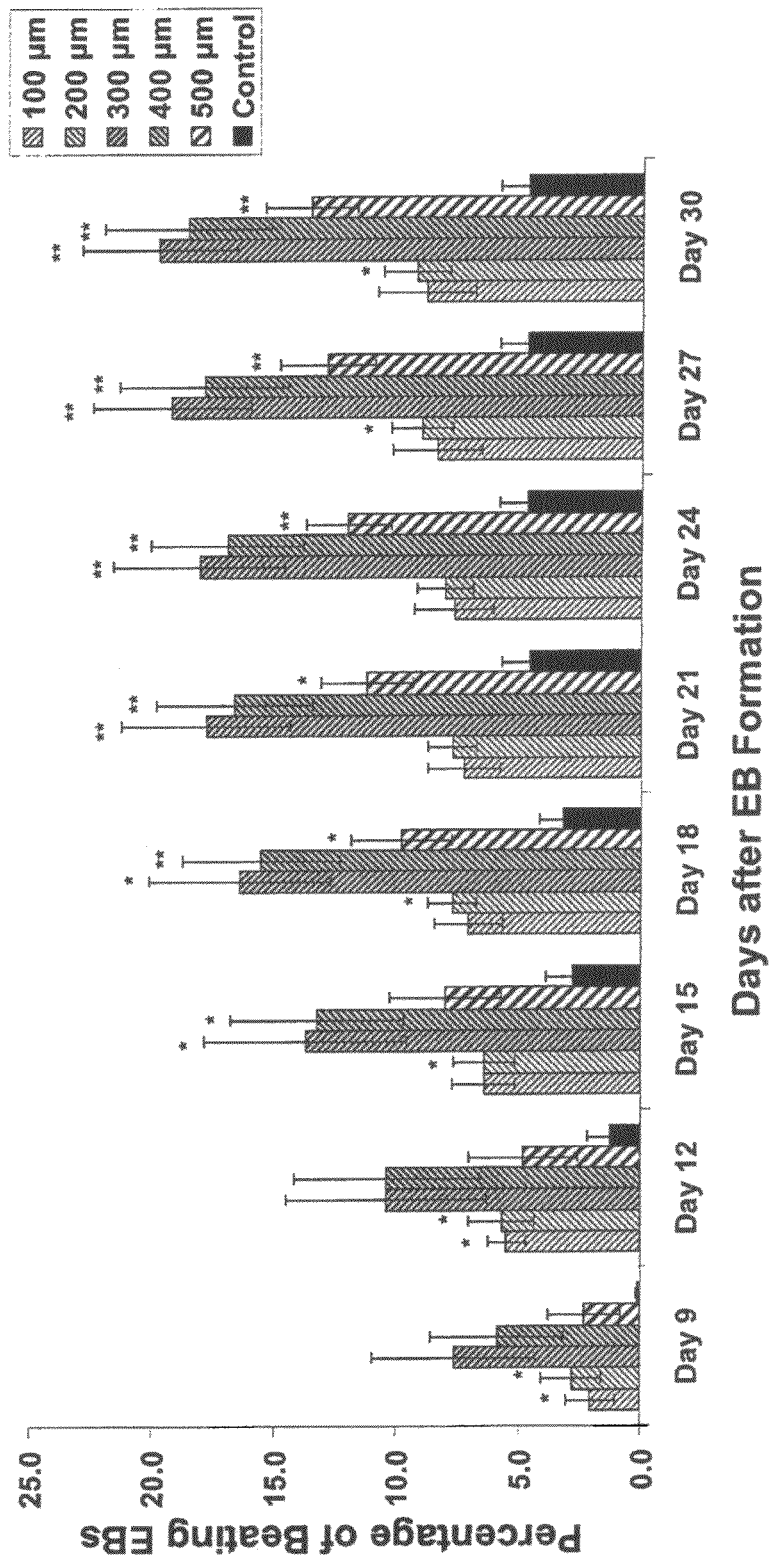
Figure 9B:
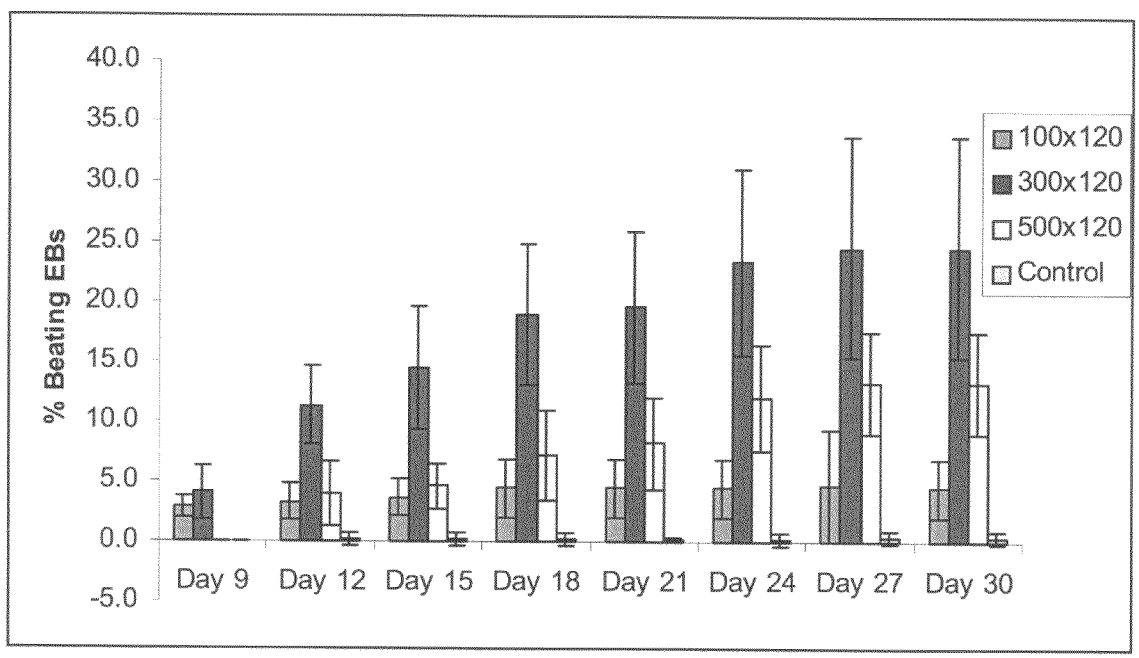

FIG. 9A-B illustrates a time course of development of spontaneously contracting hES cells (FIG. 9A) and iPS cell (FIG. 9B) EBs formed from microwells 120 μm deep×100 μm-500 μm lateral dimension and control EBs.

Figure 10:
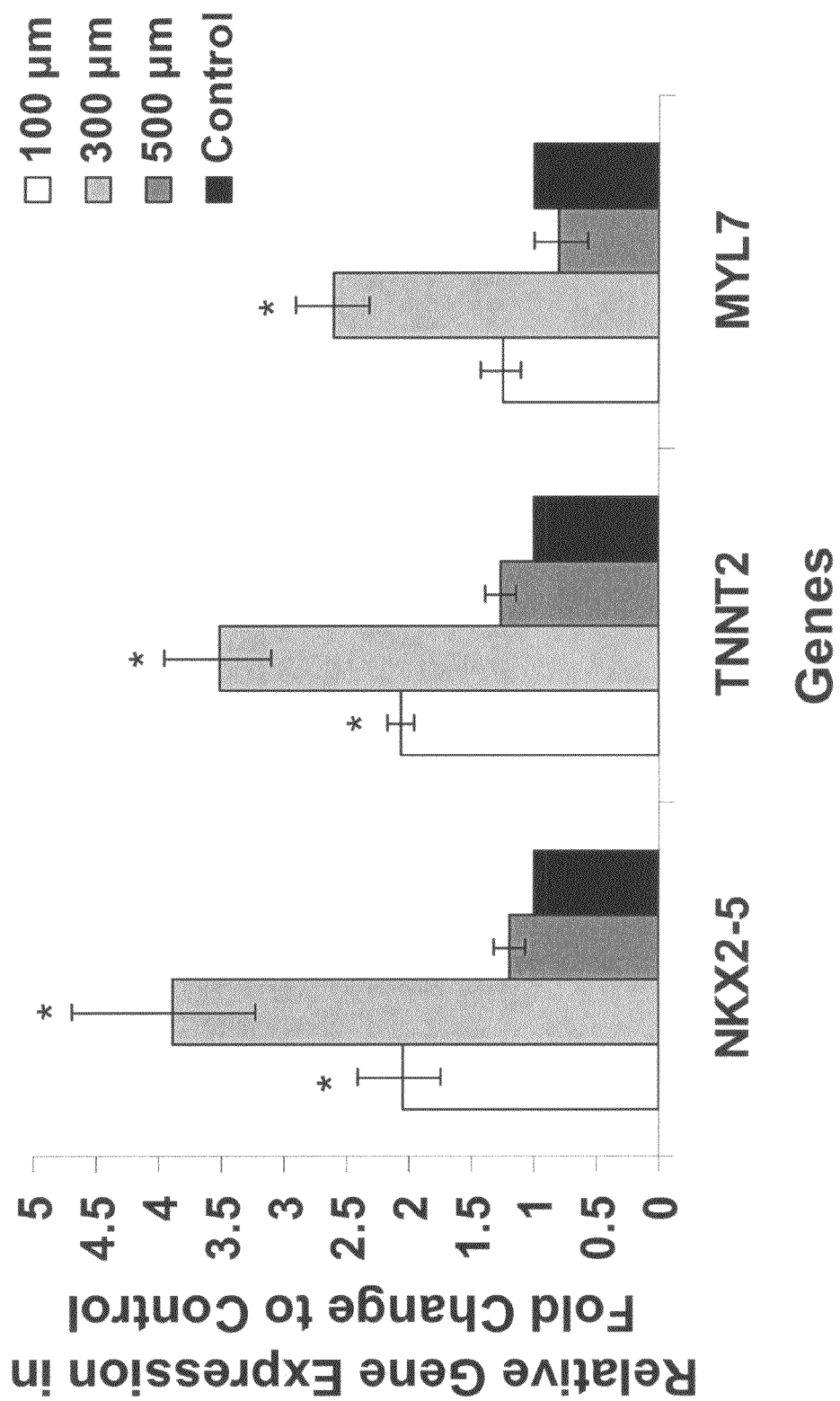

FIG. 10 illustrates the expression of the cardiac genes NKX2-5, TNNT2, and MYL7 in EBs formed from microwells 120 μm deep×100 μm, 300 μm, and 500 μm lateral dimension microwell relative to expression in control EBs.

Figure 11A:
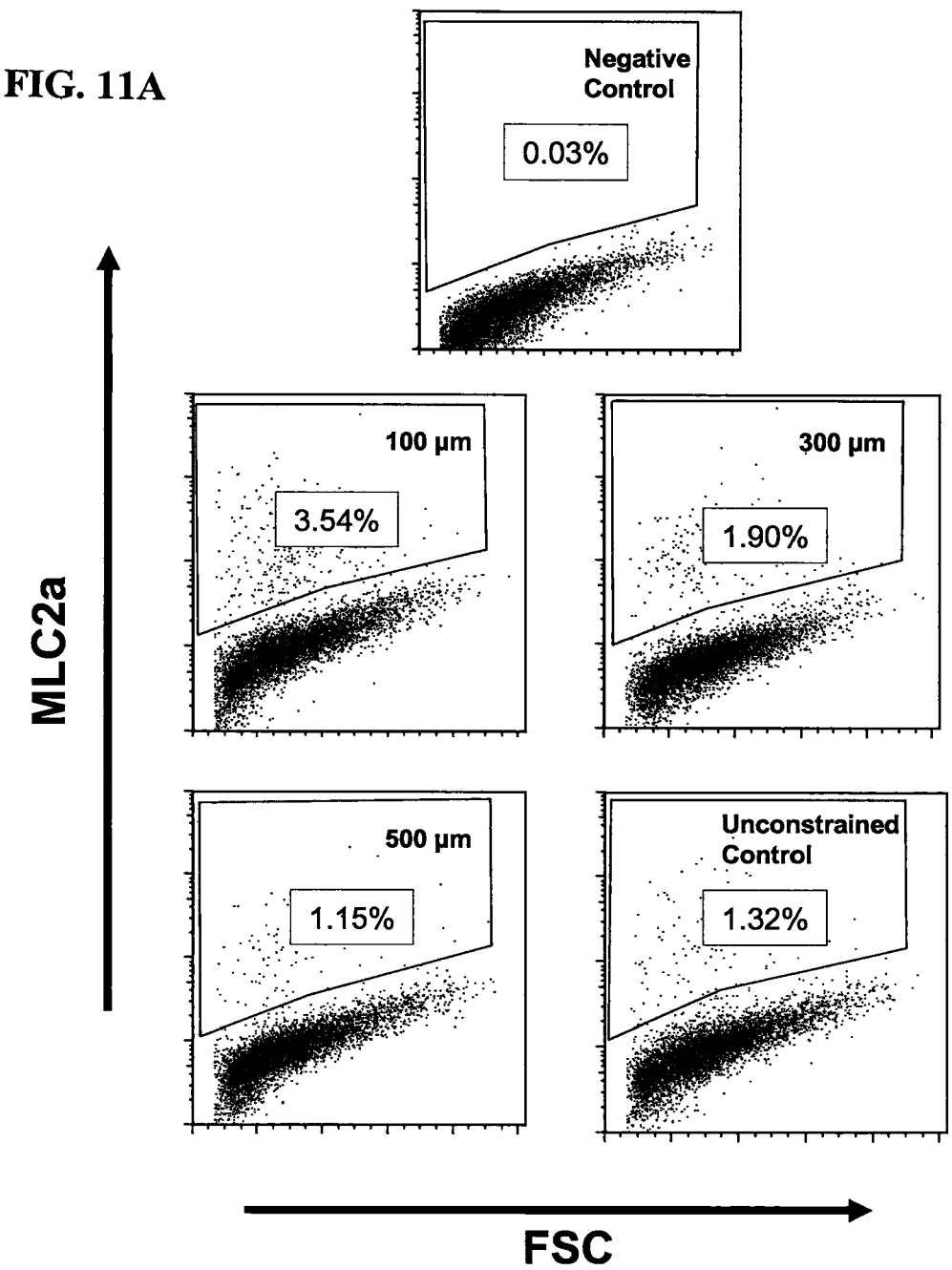
Figure 11B:
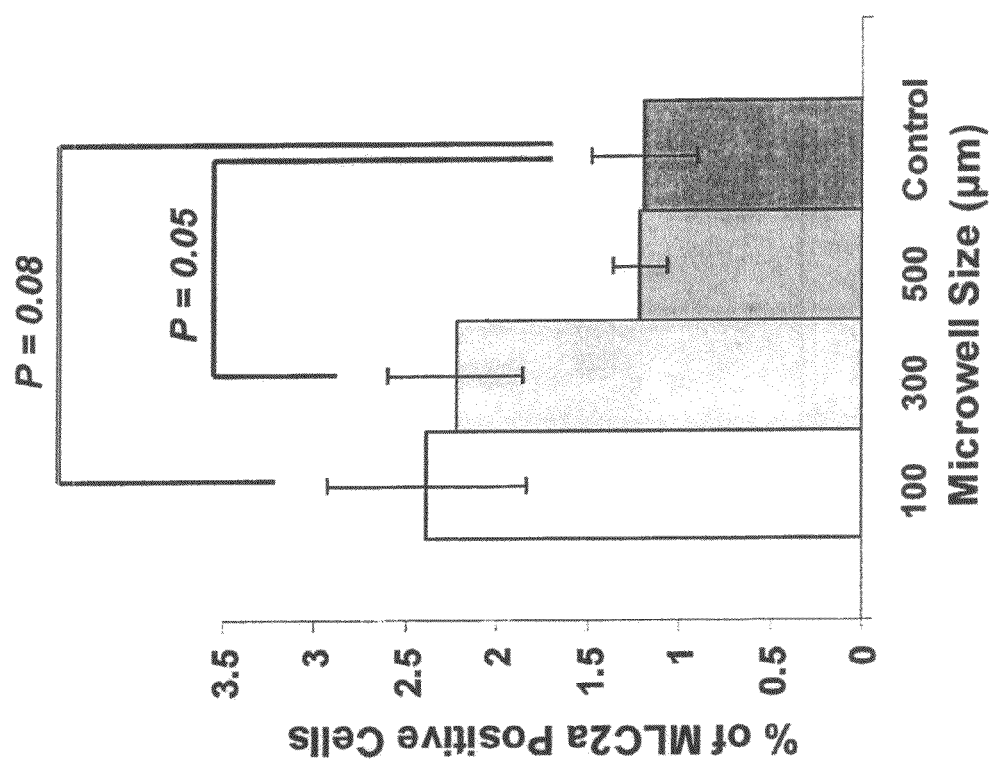

FIGS. 11A and B illustrate cells expressing a cardiac marker MLC2a from microwell and control hES cell EBs. FIG. 9A shows the scatter dot plots of flow cytometry measurement of cells harvested from EBs formed from microwells of 100 μm, 300 μm, and 500 μm lateral dimensions compared to cells from control EBs. The negative control (top panel) shows staining with the secondary antibody alone. FIG. 9B shows the average percentage of MLC2a-positive cells harvested from EBs formed from microwells of 100 μm, 300 μm, and 500 μm lateral dimensions compared to cells from control EBs. The error bars indicate the standard error of the mean.

DETAILED DESCRIPTION OF PREFERRED EMBODIMENTS

The present invention relates to the observations that size, shape and volume of undifferentiated pluripotent cell colonies often vary and that a colony's differentiation profile varies with these attributes. On the other hand, a controlled 3-D cell microenvironment, achieved by providing chemical and physical constraints on the dimensions the colonies, produces pluripotent cell colonies having a narrow size distribution, thereby allowing one to direct subsequent differentiation by controlling initial pluripotent cell colony size, shape and/or volume. The ability to sustain high density, undifferentiated pluripotent cell cultures for weeks without passaging may have valuable applications to general pluripotent cell culture techniques. Additionally, the lack of pluripotent cell differentiation after several weeks in constrained culture suggests that differentiation is tightly linked to pluripotent cell colony size or shape.

Aside from constraining pluripotent cell growth, microwell culture facilitated generation of undifferentiated cell aggregates that were easily passaged or differentiated in suspension to form EBs. As used herein, a "hES cell EB" refers to an EB formed from hES cells. Similarly, an "iPS cell EB" refers to an EB formed from iPS cells. EB size appears to influence differentiation fate, although the only reported means of controlling EB size involves enzymatically digesting pluripotent cell colonies with trypsin to single cells, and then centrifuging the desired number of cells to form a pellet [13]. Interestingly, trypsin inhibits later pluripotent cell aggregation and the cell clump formed by centrifugation is morphologically distinct from typical pluripotent cell colonies. By using microwell culture, one can define EB size without compromising cell viability or EB structure. Unlike centrifugal force aggregation methods, the microwell culture method advantageously does not employ centrifugation for aggregate or EB formation.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

The invention will be more fully understood upon consideration of the following non-limiting Examples. In the Examples, hES cell and iPS cells were cultured in microwells, and hES cell- and iPS cell-derived EBs were obtained. It is specifically contemplated that the methods disclosed are suited for primate pluripotent cells generally as pluripotent cells, regardless of their origin, operate in substantially the same manner in the disclosed methods.

EXAMPLES

Example 1

Microwells for Pluripotent Cell Culture and Embryoid Body Generation

Figure 1:
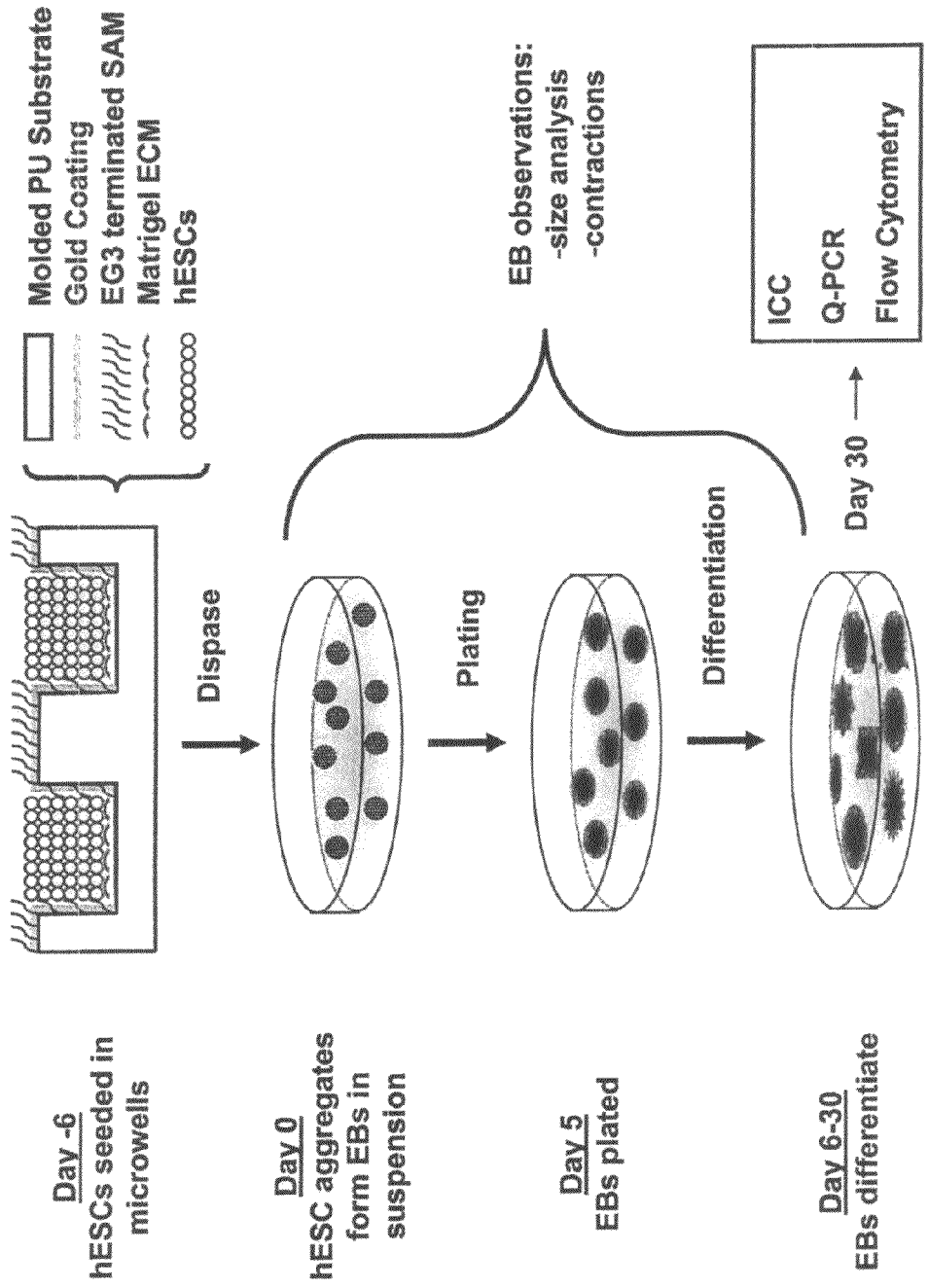
FIG. 1 illustrates a schematic of microwell controlled EB formation and differentiation.

Reference is made to FIG. 1. Microscope slides having formed thereupon a homogeneous distribution of wells of identical size and shape were constructed in three steps using a polydimethylsiloxane (PDMS) stamp to shape a surface of a UV-crosslinkable polyurethane polymer substrate. First, silicon masters, each having desired microwell patterns formed into a surface thereof, were prepared using photolithography and plasma etching techniques similar to those described by Chen et. al. [22], incorporated herein by reference as if set forth in its entirety. The surfaces were passivated by fluorination with (tridecafluoro-1,1,2,2,-tetrahydrooctyl)-1-trichlorosilane vapor. Second, a mixture of PDMS elastomer pre-polymer with curing agent (10:1) (Sylgard 184 Silicon Elastomer; Dow Corning; Midland, Mich.) was poured over silicon masters to form PDMS stamps. The mixture was degassed under vacuum and incubated overnight at 70° C. to promote polymerization. The PDMS stamps were then clipped on two sides to glass microscope slides separated by 250 μm spacers. Norland optical adhesive 61 (Norland Products Inc.; Cranbury, N.J.) pre-polymer was fed to one end of the clipped stamps and distributed via capillary action. After cross-linking under UV light for two hours, the stamps and spacers were removed, yielding patterned microwells on the slides with depths of 50 μm-120 μm and lateral dimensions of 50 μm-600 μm. Third, the surfaces of the slides were coated with gold by e-beam evaporation using oblique angles to restrict gold evaporation to the inter-well portions of the surface and to the sides of microwells. Two evaporations were performed, with slides rotated 90° between evaporations. A 80-100 Angstrom titanium layer preceded a 200-500 Angstrom gold layer evaporation. The resulting gold-treated array of microwells was semi-transparent, allowing use of light microscopy during culture. The microwells were washed in 100% ethanol and sterilized under UV light for one hour.

Slides were placed in individual wells of a 6-well culture dish with 2 ml/well of a 2 mM tri-ethylene glycol-terminated (Prochimia; Sopot, Poland) alkanethiol ethanoic SAM solution. Slides were incubated at room temperature for 2 hours and washed in 100% ethanol. All SAM solutions were stored at 4° C. and used within 1 week.

The bottoms of the microwells were then coated with a solution of growth factor-reduced Matrigel® (Beckton-Dickinson; San Jose, Calif.) by re-suspending 2 mg of Matrigel® in 12-24 ml cold DMEM/F12. About 1 ml of cold Matrigel® solution was then aliquoted to each microwell array and an additional 1 ml of DMEM/F12 was added to each sample to promote cell adhesion to the wells, where gold was not deposited. After 1 hour of incubation at 37° C., the microwells were washed once in PBS and were then transferred to non-tissue culture treated, polystyrene, 6-well plates to prevent cells from attaching to the plate surface around the microwell slides.

Pluripotent cells (hES cell lines H1 or H9, passage 20-45, WiCell Research Institute, Madison, Wis., and human iPS cell line IMR90 C4, Yu et al., Science 318:1917-1920 (2007), incorporated herein by reference as if set forth in its entirety) from wells of a 6-well plate at normal passaging confluency were treated with 1 ml/well and 0.05% trypsin, or 1 ml/well 2 mg/ml dispase in DMEM/F12 (Invitrogen; Carlsbad, Calif.) pre-warmed to 37° C. To prevent pluripotent cell colonies from dissociating to single cells, plates were monitored under a microscope, and when colony edges began to dissociate, trypsin was neutralized with 2 ml/well MEF-CM. Pluripotent cells were gently scraped from the plate, washed, filtered through a 70 µm cell strainer, and pelleted. The pellet was re-suspended in 300 µl/sample MEF-CM supplemented with 4 ng/ml bFGF (CMF+). Pluripotent cells were then seeded in aliquots onto 1-2 microwells having 50 µm or 100 µm lateral dimensions, although in subsequent experiments microwells having 600 µm lateral dimension were used, taking care to retain the entire cell solution on top of the slides. Samples were incubated for 30 minutes at 37° C. to allow pluripotent cells to settle into the microwells before adding 1.5 ml/well CMF+. The medium was changed daily thereafter and the cells typically reached confluence within a week.

Pluripotent cells localized only to the insides of the wells, as visualized by phase contrast microscopy and by Hoechst DNA-binding dye staining. The desired pluripotent cell localization was obtained in microwells having lateral dimensions ranging from 50 µm to 600 µm/side. Although bubbles appeared at the interface between the glass slide and polyurethane substrate after several days in culture, microwell integrity remained intact.

Phase contrast and epifluorescence images of differentiation data were obtained on an Olympus IX70 model microscope (Leeds Precision Instruments; Minneapolis, Minn.) using MetaVue 5.0r1 imaging software. Phase contrast, brightfield and epifluorescence images of pluripotent cell localization and viability were obtained on a Leica DM ARB microscope (Leica Microsystems; Inc., Ill.).

Figure 2:
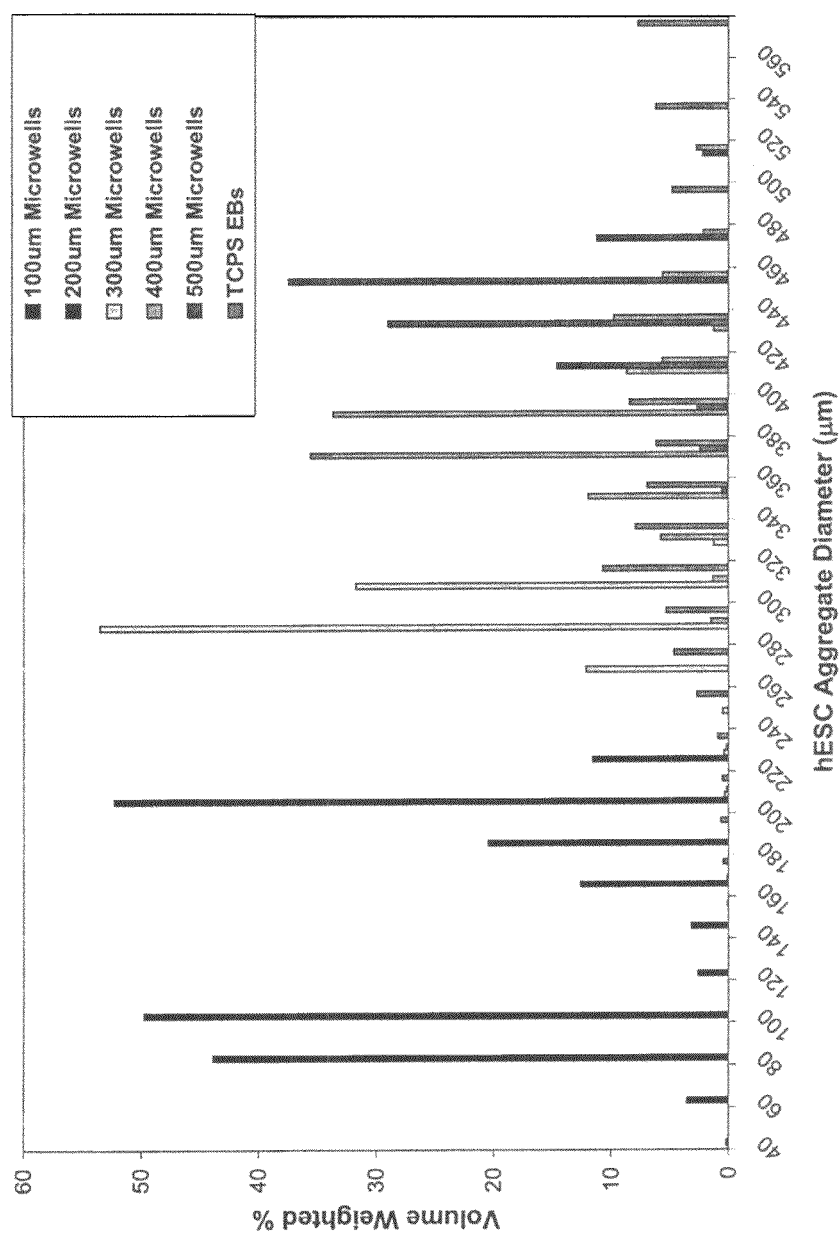
FIG. 2 depicts a normalized count of diameters of aggregates from hES cells cultured in microwells having a depth of 50 μm and lateral dimensions ranging from 100 μm to 500 μm compared to aggregates from hES cells cultured in tissue culture polystyrene (TCPS) dishes.
Figure 3:
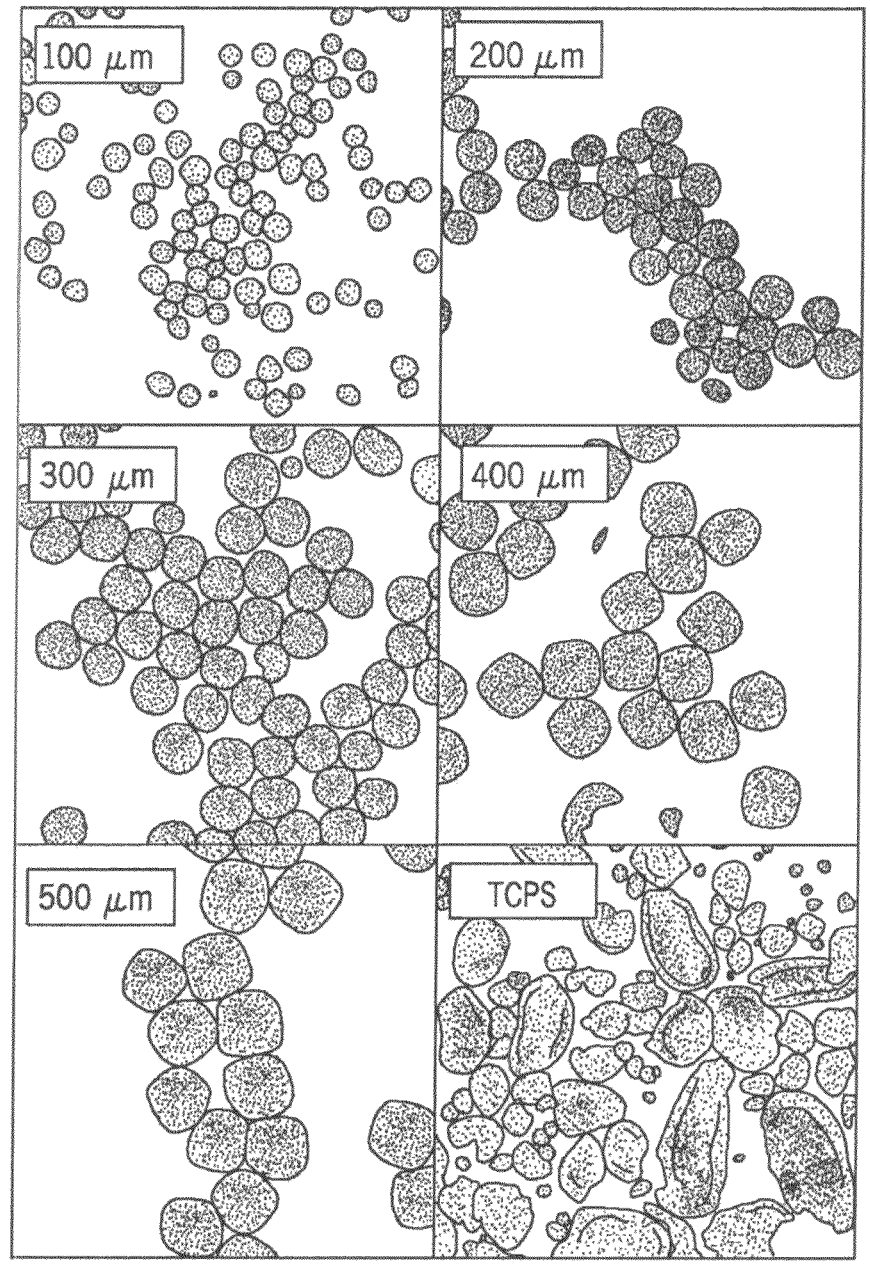
FIG. 3 are images of hES cell aggregates from microwell-cultured hES cells and from Matrigel®-cultured hES cells. hES cell aggregates were obtained from hES cells cultured 7 days in 120 μm deep×100-500 μm lateral microwells or from hES cells cultured 7 days on Matrigel® (TCPS) in CMF+. Scale bars are 300 μm.

Pluripotent cells remained viable and undifferentiated for weeks (i.e. at least 21 days) in microwells. Viability of pluripotent cells in microwells was determined by intracellular esterase activity. Live cells having constitutive intracellular esterase activity convert Calcein AM, which readily permeates cell membranes, to the polyanionic dye Calcein, which is retained within the cells and can be detected by fluorescence microscopy. Calcein AM (Molecular Probes; Carlsbad, Calif.) stock was diluted 1:1000 in PBS, aliquoted to confluent pluripotent cell microwell cultures on slides, and incubated for 30 minutes at 37° C. The slides were washed 3× and stored in PBS for analysis. As shown in FIG. 2 and FIG. 3, aggregate sizes correlated to the size of the microwell in which they were cultured. Larger microwells resulted in cells having larger dimensions.

The microwells (120 µm deep with lateral dimension of 50 µm or 100 µm) contained cells detectable by phase contrast microscopy after 19 days of culture and exhibited Calcein fluorescence. While many live cells were present in the microwells, it was not possible to quantify cell viability using Calcein fluorescence.

To verify the differentiation state of the hES cells, cells were fixed for 15 minutes in 4% paraformaldehyde in PBS with 0.4% Triton X-100. After blocking in 5% milk in PBS+ 0.4% Triton X-100 for 1 hr at 22° C., primary antibodies were prepared as a 1:200 dilution in PBS+0.4% Triton X-100 and incubated overnight at 4° C. Samples were washed 5 times in PBS before secondary antibodies diluted 1:500 in PBS+0.4% Triton X-100 were added. After 1 hour incubation at 22° C., samples were washed 3 times in PBS. The primary antibodies used for differentiation analysis were Oct3/4 (Santa Cruz Biotechnology, Inc.; Santa Cruz, Calif.) for undifferentiated hES cells, brachyury (Santa Cruz Biotechnology, Inc.) for mesodermal cells, nestin (Santa Cruz Biotechnology, Inc.) for ectodermal cells and α-fetoprotein (Biodesign International; Saco, Me.) for endodermal cells. Alexa fluor 488 or 594 conjugated secondary antibodies (Molecular Probes; Carlsbad, Calif.) were used in all cases. Qualitatively, most cells in microwells expressed Oct4. Several microwells contained multiple layers of cells that were difficult to discern by phase or fluorescence microscopy.

To quantify the differentiation state of hES cells in microwells, cells were harvested after thirteen days and eighteen days of culture. At each microwell depth (50 µm and 120 µm), two lateral dimensions, 50 µm and 100 µm, were analyzed. Cells were removed from the microwells using dispase or trypsin, then were fixed for immunocytochemistry and flow cytometric analysis. hES cells were dissociated from colonies to single cells using a 0.05% trypsin, 0.53 mM EDTA, 2% chicken serum solution. Cells were incubated 15 minutes at 37° C. and trypsin was neutralized using 2 ml/well FACS buffer (PBS without Ca/Mg$^{++}$, 2% FBS, 0.1% NaN$_3$). Oct4 expression was quantified by conventional flow cytometry [31]. Data were collected on a FACScan flow cytometer (Beckton Dickinson) and analysis was performed on CellQuest (Beckton Dickinson) and WinMDI software. All living cells were gated according to Oct-4 expression.

To compare differentiation in microwell culture to differentiation under standard culture conditions (i.e., TCPS), expression of Oct4 in hES cells plated on Matrigel® in TCPS dishes and cultured in CMF+ was determined under typical conditions for thirteen and eighteen days, without passaging. hES cells plated on Matrigel® and cultured in CMF+ 6 days prior to fixation were used as positive controls for Oct4 expression. At thirteen days, little difference in Oct4 expression was observed among microwell-cultured cells, TCPS-cultured cells and fresh hES cells. Approximately 90% of cells in each of these culture systems expressed Oct4. After eighteen days, however, clear differences appeared between hES cells cultured in TCPS dishes and those obtained from microwells. Oct4 expression of cells from microwells 50 µm deep with lateral dimensions of 50 µm or 100 µm was 90% and 91%, respectively, compared with 61% for 18-day cells under standard culture conditions (TCPS). Additionally, hES cells cultured on Matrigel®-coated TCPS dishes appeared unhealthy, and colonies were fragmented, with many dead cells floating in medium. Therefore, hES cells constrained to microwell geometries remained undifferentiated for longer periods of time than hES cells cultured in the standard TCPS dish format.

hES cells passaged from microwells to standard cultures maintain undifferentiated replication. Eighteen-day hES cell microwell cultures were enzymatically detached using 2 ml/well pre-warmed 10 mg/ml dispase in DMEM/F12 per slide. Plates were incubated for 15 to 25 minutes at 37° C., and cells were washed from microwells by pipeting. The cells on each slide were split to one well of a 6-well TCPS plate coated with Matrigel® and cultured for 5 days in CMF+ prior to immunocytochemical Oct4 expression analysis. For each microwell size and depth measured (50 µm deep with lateral dimensions of 50 µm or 100 µm, and 120 µm deep with lateral dimensions of 100 µm), undifferentiated hES cell colonies were passaged to unconstrained TCPS culture in 6-well tissue culture plates with little cell differentiation. After five days, phase contrast microscopy indicated that the unconstrained colonies were much larger than the microwell features, evidencing cell division, and had a morphology typical of colonies continuously cultured in a TCPS dish. hES cells in microwells were fixed in 4% paraformaldehyde for 15 minutes at 22° C. and were then washed 3× in PBS. Hoechst DNA-binding dye (Sigma-Aldrich; St. Louis, Mo.; 10 mg/ml aqueous stock) was diluted 1:1000 in PBS and aliquoted to microwell slides for a 5 minutes incubation at 22° C. Microwell slides were washed 2-3× and stored in PBS for epifluorescent analysis. Epifluorescent images of Oct4 expression demonstrated that the vast majority of cells harvested from microwells then cultured in a TCPS dish remained undifferentiated.

Typically, hES cell colony differentiation on Matrigel® begins in the colony interior and spreads radially as the colony grows. The differentiation of hES cells cultured in microwells then removed to unconstrained culture was sparse and occurred at the colony edges. The differentiation levels observed are otherwise typical of standard hES cell cultures on Matrigel®.

Although hES cells cultured in microwells were typically constrained to the well boundaries, by taking care to minimize shear when exchanging the culture medium, the colonies could be cultured until relatively monodisperse hES cell cell aggregates (i.e. a population of aggregates having a narrow size distribution) expanded into the medium above the microwell while remaining attached to the colonies. A typical culture term to form aggregates above microwells 50 µm deep with lateral dimension of 100 µm was 11 days. One could then readily shear the hES cell aggregates into the medium by gentle pipetting, leaving behind a confluent hES cell base layer in the microwells. If maintained in culture, this base layer replicated to fill the microwell and form a new aggregate.

To assess viability and differentiation state, aggregates were plated on Matrigel®-coated TCPS plates and cultured for 6 days in CMF+. Aggregates attached to the Matrigel® substrate and began replication within one day. hES cell growth rates were consistent with standard hES cell cultures and colonies reached passaging confluence within six days. To verify that the hES cells were undifferentiated, colonies were fixed on the sixth day and analyzed for Oct4 expression via immunocytochemistry. Very little differentiation occurred around the colony perimeter, with no visible differentiation in colony interior. This result was similar to results obtained when differentiation of entire hES cell colonies enzymatically harvested from microwells was evaluated.

hES cells were cultured on a mouse embryonic fibroblast (MEF) feeder layer in UMF+ (unconditioned hES cell medium with 4 ng/ml bFGF; see [31], incorporated herein by reference as if set forth in its entirety) in TCPS dishes for seven days, then cultured in suspension for ten days to induce differentiation and to form conventional "TCPS EBs." In addition, hES cell aggregates were cultured for 14 days in 50 µm deep×100 µm-600 µm lateral microwells in CMF+(hES cell medium conditioned on mouse embryonic fibroblasts with 4 ng/ml bFGF; see, id.), then cultured in suspension in UMF– (i.e. unconditioned hES cell medium without bFGF) in an upright T75 flask for 1 week to induce differentiation to form "microwell-derived EBs." EBs were plated on 0.1% gelatin-coated 6- or 12-well cell culture plates, cultured in UMF-supplemented with 5% FBS to facilitate attachment. After eight days, the cells were fixed and characterized.

The size distribution of EBs generated from microwell-cultured hES cell aggregates and from TCPS-harvested hES cell colonies was also examined. Individual EB diameter counts were normalized such that each count was presented as a percentage of total EBs. Microwell-derived EBs exhibited a significantly narrower size distribution than EBs derived from hES cells cocultured with MEFs on TCPS. In general, microwell derived EBs diameters correlated to the size of microwell from which the hES cells were cultured. That is, microwell-derived EBs from hES cells cultured in 100 µm had smaller diameters than microwell-derived EBs from hES cells cultured in 600 µm.

Figure 4:
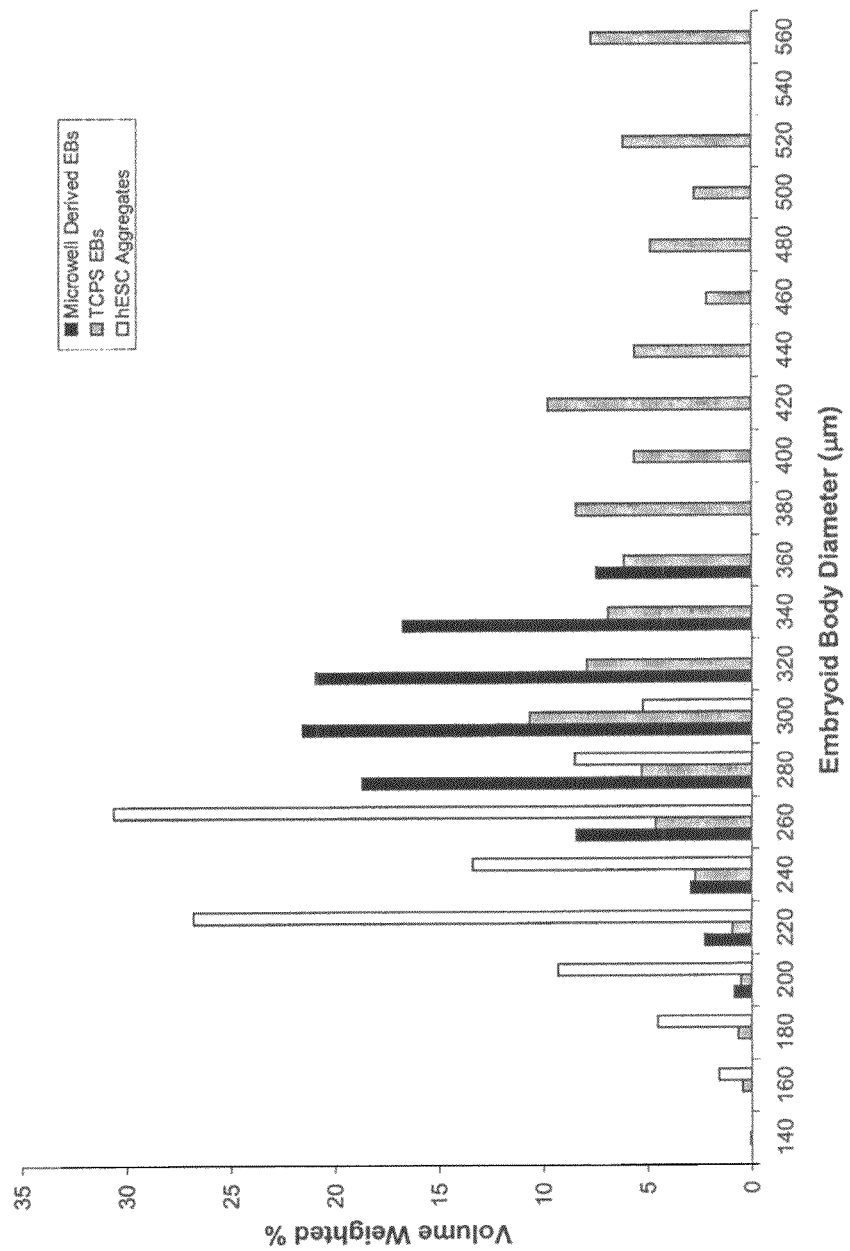
FIG. 4 depicts a volume-weighted percentage of diameters of EBs formed after conventional hES cell culture (TCPS) and after hES cell culture in microwells, as well as the volume-weighted percentage of diameters of microwell-derived hES cell aggregates.

When these data are expressed in terms of the distribution of volume weighted percentage of EBs of each diameter (FIG. 4), a more pertinent observation is revealed. By accounting for EB volume, which is proportional to the number of cells per EB, it is apparent that typical cell culture methods (which offer little control over hES cell colony size) yield a greater percentage of large EBs having substantial volumes and that the distribution of such EB sizes is very wide. In contrast, the narrow size distribution of EBs formed from the microwell-derived hES cell aggregates is maintained, as is the diameter of aggregates sheared from such cultures. This is particularly advantageous when attempting to control the parameters affecting differentiation in EBs.

hES cells in microwells, as well as aggregates released into the media, remained viable, undifferentiated and able to be passaged. Pluripotency of hES cells cultured in microwells was assessed using hES cell aggregates. EBs were cultured in two ways. First, using standard protocols, hES cell aggregates were differentiated in suspension in UMF-containing 5% FBS before plating to gelatin. Second, hES cells aggregates were differentiated by directly plating hES cell aggregates harvested from microwells onto gelatin in UMF-containing 5% FBS. Before attaching to the gelatin substrate, hES cell aggregates and EBs created from microwells exhibited a relatively monodisperse size distribution. Attachment occurred within two days of plating and EBs were cultured eight days post-attachment. In EBs cultured in suspension for one week and then for eight additional days after attachment, differentiated cultures were fixed and markers characteristic of the three embryonic germ layers using immunocytochemistry targeting the mesodermal marker α-fetoprotein, the ectodermal marker nestin and the endodermal marker brachyury were observed. Similar data were gathered for EBs plated directly to gelatin without culturing in suspension.

Example 2

Directed Differentiation of hES cells From Microwell Cultures hES cells were cultured either in microwells having depths of 50 µm-120 µm and lateral dimensions of 50 µm-500 µm or in TCPS plates as described above. Briefly, samples were incubated for 30 minutes at 37° C. to allow hES cells to settle into the microwells before adding 1.5 ml/well CMF+ to the wells of a 6-well plate. The medium was changed daily thereafter and the cells typically reached confluence within a week. TCPS EBs and microwell-derived EBS were then formed as described above.

Keratinocytes differentiation was achieved by initially forming EBs from microwell-derived hES cell aggregates as described above. EBs were grown in suspension for fourteen days in UMF− medium and then attached to gelatin-coated plates in Defined Keratinocyte Serum Free Medium (DSFM) (Invitrogen; Carlsbad, Calif.). Cells were cultured 2-3 weeks prior to analysis by immunocytochemistry and flow cytometry, as described for undifferentiated cells. Keratinocyte markers used include K14 and involucrin. Cardiomyocyte differentiation began by removing microwell-derived hES cell aggregates as described above. EBs were formed by culturing the aggregates in suspension for 1 day in UMF−, followed by culturing for 4 days in cardiac-inducing medium (UMF−, substituted with 20% serum replacer with 20% FBS). EBs were then plated to gelatin-coated TCPS dishes in cardiac-inducing medium for an additional two weeks. Cardiogenesis was monitored daily by visual inspection for spontaneously contracting (beating) regions (FIG. 9A).

With respect to the EBs differentiated into keratinocytes, the greatest percentage of keratinocytes was observed in cells obtained from microwells having smaller dimensions, such as a depth of 50 μm with lateral dimensions of 100 μm.

With respect to the EBs differentiated into cardiomyocytes, the greatest percentage of cardiomyocytes was observed in cells obtained from microwells having larger dimensions, such as a depth of 120 μm with lateral dimensions of 300-500 μm.

Example 3

Microwells for hES cells Culture and Cryopreservation hES cells were cultured in microwells having dimensions of 50 μm deep with 50 μm to 400 μm lateral dimensions as described above. Briefly, samples were incubated for 30 minutes at 37° C. to allow hES cells to settle into the microwells before adding 1.5 ml/well CMF+ to the wells of a 6-well plate. The medium was changed daily thereafter and the cells typically reached confluence within a week. Alternatively, hES cells were cultured in TCPS dishes, as described above.

After 7 days of culture, the hES cells in microwells, suspensions and TCPS plates were placed in freezers at −80° C. for up to 4 weeks. Following cryopreservation, cells frozen in suspension were thawed by immersion of the cryovial in a 37° C. waterbath with agitation. Cells were immediately diluted in 10 ml CMF (i.e. hES cell medium conditioned on mouse embryonic fibroblasts without bFGF) and centrifuged. hES cells were then diluted in 2 ml CMF and plated to 1 well of a 6-well plated pre-coated with Matrigel® and grown for six days. hES cells frozen in microwells or TCPS plates were thawed by placing the microwells or plates in a 37° C. waterbath with agitation. 3 ml CMF+ (MEF-CM with 4 ng/ml bFGF) were added to each well and then aspirated. 2 ml CMF+ were added to each well and cells were cultured for six days. After six days, cell viability was assessed by intracellular esterase activity as described above. When compared to hES cells cryopreserved on TCPS plates or cryopreserved in suspensions, hES cells cryopreserved in microwells showed significantly greater recovery efficiency at all microwell dimensions examined.

Example 4

Generation of Embryoid Bodies of Uniform Size and Predictable Cell Number

Pluripotent cells were cultured in microwells substantially as described in Example 1. Briefly, pluripotent cells from wells of a 6-well plate at normal passaging confluency were treated with 1 ml/well 1 mg/ml dispase in DMEM/F12 (Invitrogen; Carlsbad, Calif.) pre-warmed to 37° C. until colony edges began to dissociate. Cells were gently scraped off the plate and washed once in UMF−. Cells were then filtered through a strainer having a pore size of 70 μm to remove large clumps to facilitate seeding in microwell slides. Pluripotent cells were washed twice in UMF− and centrifuged to form a pellet. The pellet was then resuspended in 0.30 ml CMF+. The pluripotent cells were then seeded in aliquots into Matrigel®-coated microwells having dimensions of 120 μm deep with 100 μm-500 μm lateral dimensions, taking care to retain the entire cell solution on top of the slides. Samples were incubated for 30 minutes at 37° C. to allow pluripotent cells to settle into the microwells before adding 2 ml/well CMF+. The medium was changed daily thereafter and the cells typically reached confluence within a week.

FIG. 1 schematically depicts a general strategy for generating EBs from pluripotent cells cultured in microwells and for culturing the resulting EBs. EBs were generated from pluripotent cell colonies removed from standard tissue culture dishes, as described in Example 1, to form conventional "TCPS EBs," and from pluripotent cell colonies removed from Matrigel®-coated microwells having dimensions of 120 μm deep with 100 μm-500 μm lateral dimensions to form "microwell-derived EBs."

To initiate differentiation, microwell-cultured pluripotent cell colonies and TCPS-harvested pluripotent cell colonies were cultured in suspension in Corning 3471 ultra-low attachment 6-well plates (Coming, Inc., Lowell, Mass.) for 1 day in UMF−, followed by 4 days in a medium consisting of DMEM-F12 (Invitrogen), fetal bovine serum (20%, cardiac differentiation qualified, Hyclone, Catalog No. SH3007003, Lot No. ARH 27209), L-glutamine (2 mmol/L, Invitrogen), and 1% MEM nonessential amino acid solution (Invitrogen) ("EB medium"). The resulting EBs were plated on 0.1% gelatin-coated 6-well culture plates or coverslips in 24-well cell culture plates and cultured in EB medium for the duration of the experiment. After 7 days of differentiation in EBs, the number of attached EBs were counted using phase contrast microscopy. EBs were observed daily. After 10 days of differentiation, the FBS concentration in the EB medium was reduced to 2%.

Upon removal from microwells and after suspension culture for one day, spherical microwell-derived hES cell and iPS cell EBs formed and exhibited relatively homogeneous sizes (FIG. 5A-E; FIG. 6A-C) directly related to the initial microwell dimensions. In contrast, TCPS EBs displayed a heterogeneous size distribution (FIG. 5F; FIG. 6D).

EB size distributions were quantified using image analysis of phase contrast images with Qcapture Pro™ software (QImaging Corporation) by measuring the diameter of each EB, calculating the volume (assuming a spherical EB), and multiplying by the number of EBs of each diameter to yield the total volume of EBs for each microwell size. The cumulative volume of EBs in a given range of diameters (20 μm intervals)

was then normalized to the total EB volume in culture for each microwell size. FIGS. 7A and B present a histograms of the volume-weight distribution of EB size relative to EB diameter for each microwell size from which the EBs were produced. The average hES cell EB diameters at one day of culture for the different microwell sizes are summarized in Table 2. Note that the diameter values were calculated by Gaussian function after volume normalization and differ slightly from the average diameter values for each size of microwell EBs. Similar results were obtained with iPS cells plated into Matrigel®-coated cuboidal microwells, 100, 300, and 500 µm in lateral dimensions and 120 µm in depth.

Pluripotent cells grown in a microwell constrained culture system generated EBs with predictable and uniform-size, particularly when using microwells having dimensions of 120 µm deep with 100 µm-300 µm lateral dimensions. The data for each microwell size followed Gaussian distribution (FIGS. 7A and B). In contrast, the EBs derived from unconstrained control cultures did not have a narrow size distribution and could not be described by a simple Gaussian distribution.

TABLE 2

| Microwell Dimension (µm) | Average EB diameter (µm ± SD) |
| --- | --- |
| 120 × 100 | 88 ± 16 |
| 120 × 200 | 162 ± 24 |
| 120 × 300 | 256 ± 28 |
| 120 × 400 | 322 ± 36 |
| 120 × 500 | 350 ± 51 |
| Control (TCPS) | 196 ± 68 |

To determine if the number of cells present in EBs is directly related to the size of the microwell, microwell EBs and TCPS EBs were prepared as described above. After one day in suspension culture, individual cells from the EBs were isolated using enzymatic separation with 0.05% trypsin and counted using a hemacytometer. The average number of hES cells per EB for each microwell size is depicted in FIG. 7C. The data points were fit to a polynomial function based on the square of the X-Y dimension given that the depth of the microwells was kept constant at 120 µm. Data histograms were fit to Gaussian distributions using nonlinear least squares regression with Microcal Origin, version 7.5 (Microcal Software, Inc., Northampton, Mass.). Assuming the volume of the microwell from which an EB was produced determined cell number, the data were fit to a simple polynomial equation, cell number=A(X-Y dimension)$^2$, where A is a constant The data were well fit to the model ($R_2$=0.99) with A=0.0163±0.0004. hES cells grown in a microwell constrained culture system generated EBs with predictable and uniform cell numbers ranging from approximately 142 cells per EB to approximately 3873 cells per EB.

Microwell size affects the growth properties of EBs. Growth in culture of EBs reflects various factors, including cellular proliferation, differentiation, apoptosis, and EB disaggregation. To account for these factors, the effect of microwell size on EB dimensions was assessed following five days of suspension culture by quantifying EB size distributions using image analysis by measuring the diameter of each EB as described above. The volume-weighted percent size distributions of hES cell EBs from the different microwells followed Gaussian distributions, as indicated by the fit curves in FIG. 8A. EBs derived from 100 µm and 200 µm microwells had distinct sizes with mean diameters (±SD) of 135±37 µm and 206±44 µm, respectively. In contrast, EBs derived from 300 µm, 400 µm, and 500 µm microwell were all of similar size with mean EB diameters of 258±53 µm, 264±58 µm and 285±61 µm, respectively. Thus, EBs derived from 100 µm and 200 µm microwells tended to grow in size during five days of suspension culture, while EBs derived from 300 µm, 400 µm, and 500 µm microwell either did not increase in size or slightly decreased. EBs formed from iPS cells showed comparable changes in size during culture (FIG. 8B).

Example 5

Increasing Cardiogenesis in EBs by Regulating Microwell Size

EBs were generated from pluripotent cells cultured in microwells having dimensions of 120 µm deep with 100 µm-500 µm lateral dimensions essentially as described in Example 4. To induce differentiation, pluripotent cell aggregates were removed from the microwells after six days in culture with CMF+. The colonies were cultured in suspension for one day in UMF−, followed by four days in suspension in EB medium. EBs were then attached to gelatin-coated plates and cultured in EB medium for a total of 30 days. EBs were observed daily, and the total EBs as well as contracting EBs were counted using phase contrast microscopy every three days. The percentage of contracting EBs was obtained by dividing the number of contracting EBs by the total number of EBs. Data are presented as mean and standard error of the mean (SEM) and the two-tailed Student's t-test was used for comparison of two groups with p<0.05 considered significant.

Contracting EBs in the microwell and unrestrained control EB cultures first appeared within three days of plating on gelatin coated plates, and the fraction of contracting EBs increased over time to reach a plateau at approximately 21 days (FIGS. 9A and B). Approximately ~18-20% of EBs produced from 300 µm and 400 µm microwells displayed signs of spontaneous contraction after 30 days of culture on gelatin-coated plates compared to ~8-10% contracting EBs produced from 100 µm and 200 µm microwells and 14% contracting EBs produced from 500 µm microwells. EBs produced from unconstrained control culture conditions yielded only 5% contracting EBs, significantly less than all of the microwell EBs except for those produced from 100 µm microwells.

To determine the expression of genes specific for cardiac cells, real-time quantitative polymerase chain reaction (PCR) was performed using RNA from EBs that had been in culture for 30 days. Total RNA from single wells of an EB culture in 6-well plate was isolated by first homogenizing the EBs in 1 ml Trizol® Reagent (Invitrogen, Carlsbad, Calif.). The RNA phase was separated from the homogenate by adding 0.2 ml chloroform and subsequent centrifugation for 15 min at 12000 rpm at 4° C. The aqueous supernatant containing the RNA phase was collected and RNA precipitated using 0.5 ml 2-propanol followed by a 10 minute incubation at room temperature. The RNA precipitate was centrifuged for 10 minutes at 12000 rpm at 4° C. The supernatant was discarded and the RNA pellet was washed in 1 ml of 75% ethanol, vortexed, and centrifuged for 5 min at 7500 rpm at 4° C. The RNA pellet was air-dried and resuspended in 30 µl water. The concentration of RNA was determined by using a UV spectrophotometer to measure absorbance at 260 nm and 280 nm. 2 µg of total RNA was subjected to a reverse transcription (RT) reaction using High-Capacity cDNA Archive Kit (Applied Biosystems, Foster City, Calif.). Each PCR was performed in triplicates with TaqMan® Universal PCR Kit and TaqMan® Gene Expression Assays (both obtained from Applied Biosystems). Taq- Man Primers for GAPDH, NKX2-5, cardiac troponin T (TNNT2), myosin light chain 2a were used (Table 3.) The gene expression relative to the control was calculated using the comparative Ct method as described in Livak and Schmittgen, Methods 25:402-408 (2001), incorporated herein by reference as if set forth in its entirety. Data are presented as mean and standard error of the mean (SEM) and the two-tailed Student's t-test was used for comparison of two groups with $p<0.05$ considered significant.

TABLE 3

| Name | Gene Symbol | Function | TaqMan ® Primers |
|---|---|---|---|
| Glyceraldehyde-3-Phosphate Dehydrogenase | GAPDH | House-keeping gene | Hs99999905_m1 |
| NK2 Transcription Factor Related, Locus 5 | NKX2.5 | Transcription factor critical for cardiac development | Hs00231763_m1 |
| Cardiac Troponin T | TNNT2 | Cardiac specific myofilament protein | Hs00165960_m1 |
| Myosin Light Chain 2a | MYL7 | Cardiac myofilament protein | Hs00165960_m1 |

The expression of NKX2.5, TNNT2, and MYL7 was compared between EBs generated from 100 μm, 300 μm, and 500 μm microwells and control EBs. The greatest fold increase (2-4 fold) of expression of NKX2-5, TNNT2, and MYL7 compared to control was found in EBs generated in 300 μm microwells (FIG. 10). The 100 μm microwell EBs showed a significant 1-2 fold increase in expression in comparison to control EBs. Overall, the quantitative PCR data were consistent with the measurements of percentage of contracting EBs in suggesting that microwell EBs can undergo cardiogenesis more efficiently than EBs formed under standard conditions, and that 300 μm microwells promote most strongly the expression of cardiac markers.

To examine the effect of microwell size on the total number of cardiomyocytes formed within a microwell, flow cytometry was used to determine the number of cells expressing cardiac-specific proteins. EBs derived from microwells of 100 μm, 300 μm, and 500 μm lateral dimensions and control EBs from standard unconstrained culture following 30 days of differentiation were enzymatically separated into single cells by washing twice in 2 ml/well PBS for 5 minutes at 37° C. followed by incubation in 1 ml/well of 0.25% trypsin, 0.53 mM EDTA, 2% chick serum in a 6-well plate for 10 min at 37° C., followed by neutralization using 4 ml/well FACS buffer (PBS without Ca/Mg$^{2+}$, 2% FBS, 0.1% NaN$_3$). Any remaining cell aggregates were disrupted by gently pipetting using a 5 ml pipette. Cells were centrifuged for 5 minutes at 1000 rpm at room temperature, the supernatant was discarded, and the pellet was resuspended in 1 ml PBS with 60 μl of 16% paraformaldehyde for fixation. The samples were incubated for 10 minutes in a 37° C. water bath and then chilled on ice for 1 minute. The samples were centrifuged, the pellet was resuspended in 1 ml of ice-cold 90% methanol, and incubated on ice for 30 minutes to permeabilize the cells. Cells were washed once in FACS buffer containing 0.1% Triton, centrifuged, and the supernatant was discarded leaving approximately 50 μl of each sample.

The primary antibodies recognizing sarcomeric myosin (MF20, Developmental Studies Hybridoma Bank, Iowa City, Iowa) and recognizing a ubiquitous myofilament protein expressed in all early cardiomyocyte types (anti-MLC2a, Synaptic Systems, Germany, Cat. No. 311011) were diluted 1:20 and 1:400, respectively, in 0.1% Triton X-100, 1% BSA in PBS and aliquoted to each sample for a total sample volume of 100 μl. The samples were incubated overnight at 4° C. The samples were washed twice in 3 ml FACS buffer plus Triton, centrifuged, and the supernatant was discarded retaining an approximate sample volume of 50 μl. The secondary antibody, Alexa Fluor 633 goat anti-mouse IgG2b (Invitrogen), was diluted 1:1000 in 50 μl/sample FACS buffer plus Triton (0.1%) and aliquoted to each sample to a final sample volume of 100 μl. Samples were incubated for 30 to 45 minutes in the dark at room temperature and then washed twice in FACS buffer. Samples were centrifuged, resuspended in 300 μl FACS buffer, transferred to flow cytometry tubes, and stored on ice until analysis. The data was collected on a FACSCaliber™ flow cytometer (Becton Dickinson, Franklin Lakes, N.J.) and the analysis was performed using CellQuest™ software (Becton Dickinson). All cells were gated according to light scatter and fluorescence. The data are presented as mean and standard error of the mean (SEM) and the two-tailed Student's t-test was used for comparison of two groups with $p<0.05$ considered significant.

The top panel of FIG. 11A shows cells stained with the secondary antibody alone and the remaining panels show cells from different sources of EBs stained with anti-MLC2a and the secondary antibody. The data were obtained from samples composed of a collection of EBs from a single well of a 6-well plate containing 50-200 EBs (contracting and non-contracting) for each experiment. In this collection of cells, the number of MLC2a-positive cells isolated from control EBs was generally in the range of one percent (FIGS. 11A and B), reflecting the well-known inefficiency of standard EB protocols to generate cardiac myocytes. Evaluation of EBs from the different sized microwells revealed that 500 μm microwells generated a similar number of MLC2a-positive cells (~1.2%) when compared to control EBs. In contrast, the 100 μm and 300 μm microwells produced on average approximately twice as many cardiomyocytes (~2.4%) (FIGS. 11A and B). Interestingly, the 100 μm microwell EBs produced as many or more cardiomyocytes as the 300 μm microwell EBs, which is surprising in light of the finding that the 300 μm microwell EBs formed about twice as many contracting EBs compared to 100 μm EBs. This apparent discrepancy may be explained by differences in the size of contracting areas in EBs, the presence of cardiomyocytes in noncontracting EBs, or technical limitations in the flow cytometry assay. Similar results were obtained when using the MF20 as the primary antibody.

To examine the spatial distribution of cardiomyocytes in the differentiating EBs, immunolabeling for cardiac proteins in beating EBs was performed to identify all hES cell-CMs using antibodies to sarcomeric myosin (MF20) and MLC2a. At day 30 after plating on gelatin coated coverslips, EBs were fixed in 4% paraformaldehyde by diluting 16% paraformaldehyde (EMS Catalog No. 15710-S) in 1×PBS (Invitrogen, Catalog No. 14190-144) and incubating for 15 minutes at room temperature. The samples were rinsed twice in PBS after fixation, followed by cell permeabilization in 0.2% Triton X-100 in PBS solution (Sigma, Catalog No. T-9284) for 1 hour at room temperature. The samples were blocked by preparing a fresh solution of 5% non-fat dry milk in 0.2% Triton X-100 and incubating for two hours at room temperature on a at speed setting of 2 (Roto-Shake Genie™, Scientific Industries, Inc.). The samples were then washed twice with PBS for 5 minutes per wash. The primary antibodies MF20 (Developmental Studies Hybridoma Bank) and anti-MLC2a (Synaptic Systems) were diluted 1:20 or 1:400, respectively, in 0.1% Triton X-100, 1% BSA in PBS solution. The antibodies were applied to the samples and incubated overnight at 4° C. The samples were then washed with 0.2% Tween 20 in PBS three times for 5 minutes per wash, and washed once in 1×PBS. The secondary antibody, Alexa Fluor 594 goat anti-mouse IgG2b (Invitrogen), was diluted in the same solution as the primary antibody and incubated at room temperature for 1.5 hours in the dark. Three 5-minute washes in 0.2% Tween 20 in PBS were followed by one 1×PBS wash. One drop of antifade reagent with DAPI (ProLong® Gold, Invitrogen, Catalog No. P36935) was placed on each slide and coverslips were mounted. The cells were analyzed using epifluorescence microscopy.

Approximately 5-20% of the EBs stained with MF20 or anti-MLC2a exhibited immunolabeling for the cardiac proteins, which is consistent with the percentage of contracting EBs observed in culture. Within the EBs, cells positive for MF20 or anti-MLC2a staining were tightly clustered, consistent with the localized regions of contraction observed in EBs. Typically, only a single outgrowth of cardiomyocytes was observed for an EB with the exception of some large EBs that contained multiple regions. Staining of beating EBs from 100 µm, 300 µm, and 500 µm microwells with MF20 or anti-MLC2a demonstrated that beating EBs formed from 100 µm microwell cultures were small, but dense in cardiomyocytes, which often constituted the majority of the cells in the EB. At least more than about 50%, often more than about 60% or about 70% or about 80% or about 90% or substantially all of the cells in beating EBs expressed cardiac proteins. In contrast, larger EBs such as those formed from 300 µm and 500 µm microwells contained a low number of cardiomyocytes and these cells constituted only a small fraction of cells within the EB. These data demonstrate that the size of microwells used to form EBs can strongly impact the efficiency of cardiac differentiation. Particularly, EBs formed from 100 µm microwells are greatly enriched in cardiomyocytes relative to other cell types.

The present invention has been described in connection with what are presently considered to be the most practical and preferred embodiments. However, the present invention has been presented by way of illustration and is not intended to be limited to the disclosed embodiments. Accordingly, those skilled in the art will realize that the present invention is intended to encompass all modifications and alternative arrangements within the spirit and scope of the invention as set forth in the appended claims.

Cited Documents

[1] Reubinoff B, et al., "Embryonic stem cell lines from human blastocysts: somatic differentiation in vitro," Nat. Biotechnol. 18:399-404 (2000).

[2] Odorico J, et al., "Multilineage differentiation from human embryonic stem cell lines," Stem Cells 19:193-204 (2001).

[3] Thomson J, et al., "Embryonic stem cell lines derived from human blastocysts," Science 282:1145-1147 (1998).

[4] Spradling A, et al., "Stem cells find their niche," Nature 414:98-104 (2001).

[5] Streuli C, "Extracellular matrix remodelling and cellular differentiation," Curr. Opin. Cell Biol. 11:634-40 (1999).

[6] Watt F & Hogan Bm "Out of Eden: stem cells and their niches," Science 287:1427-1430 (2000).

[7] Schuldiner M, et al., "Effects of eight growth factors on the differentiation of cells derived from human embryonic stem cells," Proc. Natl. Acad. Sci. USA 97:11307-11312 (2000).

[8] Itskovitz-Eldor J, et al., "Differentiation of human embryonic stem cells into embryoid bodies compromising the three embryonic germ layers," Mol. Med. 6:88-95 (2000).

[9] Dvash T & Benvenisty N, "Human embryonic stem cells as a model for early human development," Best Pract. Res. Clin. Obstet. Gynaecol. 18:929-940 (2004).

[10] Tian X, et al., "Cytokine requirements differ for stroma and embryoid body-mediated hematopoiesis from human embryonic stem cells," Exp. Hematol. 32:1000-1009 (2004).

[11] Wang L, et al., "Endothelial and hematopoietic cell fate of human embryonic stem cells originates from primitive endothelium with hemangioblastic properties," Immunity 21:31-41 (2004).

[12] Falconnet D, et al., "Surface engineering approaches to micropattern surfaces for cell-based assays," Biomaterials 27:3044-3063 (2006).

[13] Ng E, et al., Forced aggregation of defined numbers of human embryonic stem cells into embryoid bodies fosters robust, reproducible hematopoietic differentiation," Blood 106:1601-1603 (2005).

[14] Lussi J, et al., "Pattern stability under cell culture conditions—a comparative study of patterning methods based on PLL-g-PEG background passivation," Biomaterials 27:2534-2541 (2006).

[15] Suh K, et al., "A simple soft lithographic route to fabrication of poly(ethylene glycol) microstructures for protein and cell patterning. Biomaterials 25:557-563 (2004).

[16] Luk Y, et al., "Self-assembled monolayers of alkanethiolates presenting mannitol groups are inert to protein adsorption and cell attachment," Langmuir 16:9604-9608 (2000).

[17] Lehnert D, et al., "Cell behaviour on micropatterned substrata: limits of extracellular matrix geometry for spreading and adhesion," J. Cell Sci. 117:41-52 (2004).

[18] Mrksich M, et al., "Controlling cell attachment on contoured surfaces with self-assembled monolayers of alkanethiolates on gold," Proc. Natl. Acad. Sci. USA 93:10775-10778 (1996).

[19] Mrksich M, "Tailored substrates for studies of attached cell culture," Cell Mol. Life Sci. 54:653-662 (1998).

[20] Chen C, et al., "Geometric control of cell life and death," Science 276:1425-1428 (1997).

[21] Clare T, et al., "Functional monolayers for improved resistance to protein adsorption: oligo(ethylene glycol)-modified silicon and diamond surfaces," Langmuir 21:6344-6355 (2005).

[22] Chen C, et al., "Using self-assembled monolayers to pattern ECM proteins and cells on substrates," Methods Mol. Biol. 139:209-219 (2000).

[23] Chen C, et al., "Micropatterned surfaces for control of cell shape, position, and function," Biotechnol. Prog. 14:356-363 (1998).

[24] Whitesides G, et al., "Soft lithography in biology and biochemistry," Annu Rev. Biomed. Eng. 3:335-373 (2001).

[25] Chen C, et al., "Micropatterned surfaces for control of cell shape, position, and function," Biotechnol. Prog. 14:356-363 (1998).

[26] Mrksich M, et al., "Using microcontact printing to pattern the attachment of mammalian cells to self-assembled monolayers of alkanethiolates on transparent films of gold and silver," Exp. Cell Res. 235:305-313 (1997).

[27] Singhvi R, et al., "Engineering cell shape and function," Science 264:696-698 (1994).

[28] Xu C, et al., "Feeder-free growth of undifferentiated human embryonic stem cells," Nat. Biotechnol. 19:971-974 (2001).

[29] Dusseiller M, et al., "An inverted microcontact printing method on topographically structured polystyrene chips for arrayed micro-3-D culturing of single cells," Biomaterials 26:5917-5925 (2005).

[30] Chin V, et al., "Microfabricated platform for studying stem cell fates," Biotechnol. Bioeng. 88:399-415 (2004).

[31] Ji L, et al., "Cryopreservation of adherent human embryonic stem cells," Biotechnol. Bioeng. 88:299-312 (2004).

[32] Saha S, et al., "Inhibition of human embryonic stem cell differentiation by mechanical strain," J. Cell Physiol. 206: 126-137 (2006).

[33] Noaksson K, et al., "Monitoring differentiation of human embryonic stem cells using realtime PCR," Stem Cells 23:1460-1467 (2005).

[34] Wei H, et al., "Embryonic stem cells and cardiomyocyte differentiation: phenotypic and molecular analyses," J. Cell Mol. Med. 9:804-817 (2005).

[35] Sidhu K & Tuch B, "Derivation of three clones from human embryonic stem cell lines by FACS sorting and their characterization," Stem Cells Dev. 15:61-69 (2006).

[36] Orner B, et al., Arrays for the combinatorial exploration of cell adhesion," J. Am. Chem. Soc. 126:10808-10809 (2004).

[37] Anderson D, et al., "Nanoliter-scale synthesis of arrayed biomaterials and application to human embryonic stem cells," Nat. Biotechnol. 22:863-866 (2004).

[38] Mohr J, et al., "3-D microwell culture of human embryonic stem cells," Biomaterials 27:6032-6042 (2006).

We claim:

1. A method for culturing human pluripotent stem cells to obtain a contracting embryoid body in which at least 50% of cells of the contracting embryoid body express MF20 or MLC2a, the method comprising the steps of:

harvesting aggregates or colonies of substantially undifferentiated human pluripotent stem cells from a microwell that constrains the growth of the human pluripotent stem cells in three dimensions and having a lateral dimension of about 100 microns;

differentiating the harvested aggregates or colonies of pluripotent stem cells under unconstrained culture conditions for a period sufficient to form a population of embryoid bodies comprising a plurality of contracting embryoid bodies, wherein at least 50% of the cells of each contracting embryoid body of the plurality express MF20 or MLC2a.

2. The method of claim 1, wherein the population of embryoid bodies have a substantially uniform size and shape.

3. The method of claim 1, wherein each embryoid body comprises a substantially uniform number of cells.

4. The method of claim 1, wherein the microwell is rectangular.

5. The method of claim 1, wherein the microwell has a depth between about 10 microns and about 1000 microns.

6. The method of claim 1, wherein the harvesting step comprises shearing the pluripotent stem cells from the microwell.

7. The method of claim 1, wherein the dimension-constrained microwell has cell-attracting and cell-repulsing portions.

* * * * *